(12) United States Patent
Jinno

(10) Patent No.: US 10,869,710 B2
(45) Date of Patent: Dec. 22, 2020

(54) TREATMENT DEVICE

(71) Applicant: TERUMO KABUSHIKI KAISHA, Tokyo (JP)

(72) Inventor: Makoto Jinno, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 683 days.

(21) Appl. No.: 15/445,803

(22) Filed: Feb. 28, 2017

(65) Prior Publication Data

US 2017/0245910 A1 Aug. 31, 2017

(30) Foreign Application Priority Data

Feb. 29, 2016 (JP) ................... 2016-038101

(51) Int. Cl.
*A61B 18/08* (2006.01)
*A61B 17/00* (2006.01)
(Continued)

(52) U.S. Cl.
CPC ...... *A61B 18/082* (2013.01); *A61B 17/00008* (2013.01); *A61B 17/32* (2013.01); *A61B 18/1482* (2013.01); *A61B 2017/00778* (2013.01); *A61B 2018/00404* (2013.01); *A61B 2018/00428* (2013.01); *A61B 2018/00595* (2013.01); *A61B 2018/00601* (2013.01)

(58) Field of Classification Search
CPC .............. A61B 17/00008; A61B 17/32; A61B 17/320016; A61B 2017/320056; A61B 2017/00778; A61B 2018/00428; A61B 2018/00571; A61B 2018/00589; A61B 2018/00595; A61B 2018/00601; A61B 2018/00607; A61B 2018/00982; A61B 18/04; A61B 18/08; A61B 18/082
See application file for complete search history.

(56) References Cited

U.S. PATENT DOCUMENTS 6,193,653 B1  2/2001  Evans et al.
7,981,127 B2  7/2011  Kasahara et al.
(Continued)

FOREIGN PATENT DOCUMENTS

JP   2003-199765 A   7/2003
WO  2007/021010 A1  2/2007

OTHER PUBLICATIONS

Office Action (Notice of Reasons for Refusal) dated Jul. 19, 2019, by the Japanese Patent Office in corresponding Japanese Patent Application No. 2016-038101 and an English Translation of the Office Action. (10 pages).

*Primary Examiner* — Ronald Hupczey, Jr.
*Assistant Examiner* — Bradford C. Blaise
(74) *Attorney, Agent, or Firm* — Buchanan Ingersoll & Rooney PC

(57) ABSTRACT

A treatment device is disclosed, which includes a dissecting section main body which is configured to dissect tissue in a living body when inserted into the living body along a blood vessel, and which has a slit permitting a branch vessel branched from the blood vessel to enter into the slit, a stanching section which is disposed at the slit and which presses and cauterizes the branch vessel introduced into the slit, and a cutting section which is disposed at the slit and which cuts the cauterized branch vessel.

20 Claims, 22 Drawing Sheets

(51) Int. Cl.
*A61B 18/14* (2006.01)
*A61B 17/32* (2006.01)
*A61B 18/00* (2006.01)

(56) References Cited

U.S. PATENT DOCUMENTS

2003/0065323 A1* 4/2003 Hess ................ A61B 17/00008
606/49
2003/0130654 A1 7/2003 Kasahara et al.
2005/0096671 A1* 5/2005 Wellman .......... A61B 17/00008
606/139
2006/0276815 A1* 12/2006 Lotti ................ A61B 17/00008
606/159
2008/0208193 A1 8/2008 Yamatani et al.

* cited by examiner

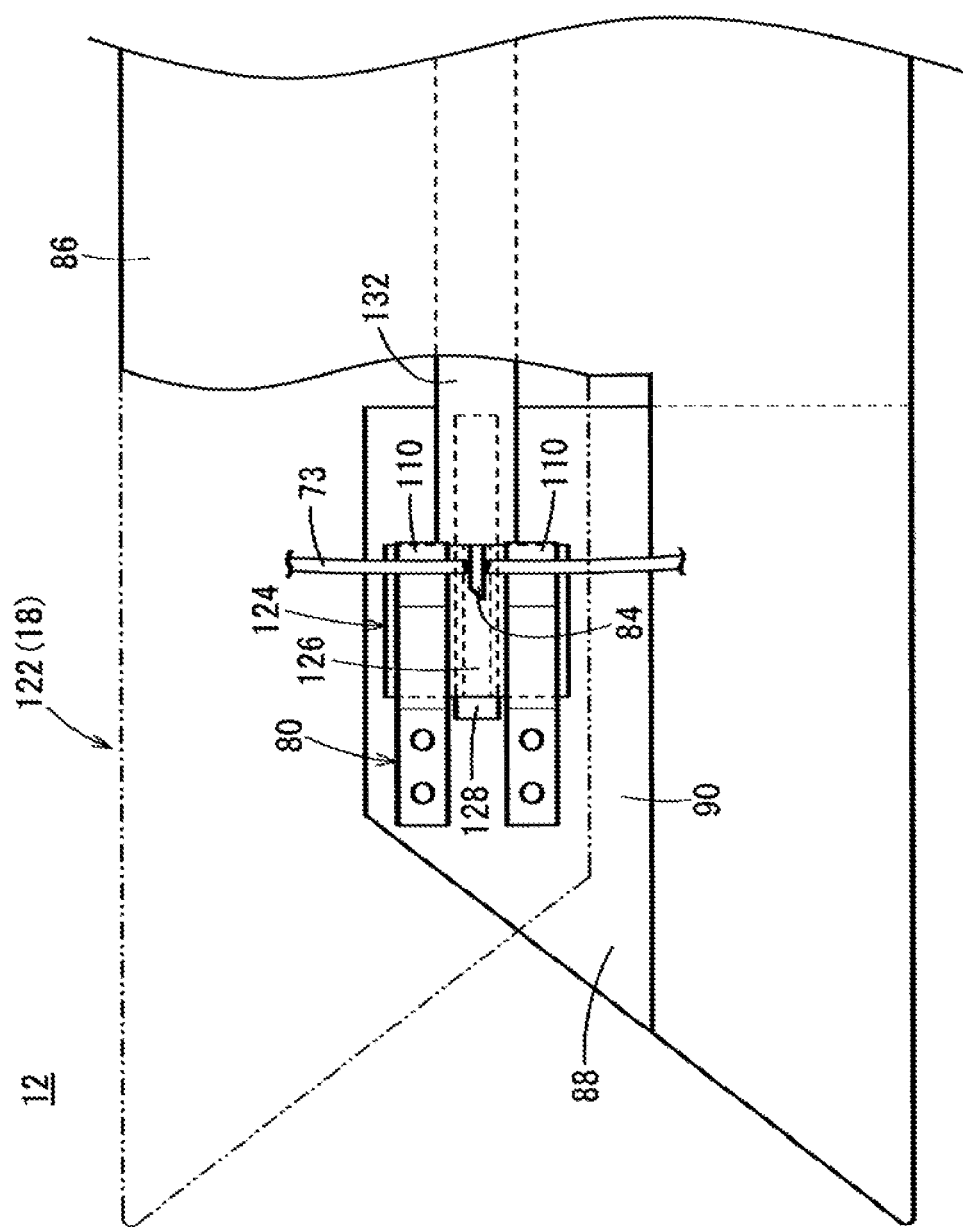

TREATMENT DEVICE

CROSS-REFERENCES TO RELATED APPLICATIONS

This application claims priority to Japanese Patent Application No. 2016-038101 filed on Feb. 29, 2016, the entire content of which is incorporated herein by reference.

TECHNICAL FIELD

The present disclosure relates to a treatment device for dissecting tissue such as fat in a living body and stanching and cutting a blood vessel.

BACKGROUND DISCUSSION

It is known to use an artery graft represented by internal thoracic artery, gastroepiploic artery and radial artery or a vein graft represented by great saphenous vein as a bypass vessel in performing vascular bypass grafting at the heart (coronary artery bypass grafting: CABG). It has been reported that artery grafts (particularly, internal thoracic artery) offer higher long-term patency rates than vein grafts.

Thus, vein grafts are commonly said to be poor in long-term patency rate. In recent years, however, it has been reported that the long-term patency rate concerning a vein graft is enhanced when the vein graft is harvested in the state of being covered with the surrounding tissue (for example, fat, connective tissue, tissue between a skin layer and a muscle layer, tissue between a skin layer and an interosseous membrane, branch vessels, etc.) and is used as a bypass vessel while remaining covered with the tissue.

U.S. Pat. No. 7,981,127 discloses a system by which a blood vessel in a living body can be harvested endoscopically.

In using the system disclosed in U.S. Pat. No. 7,981,127, however, a blood vessel and the surrounding tissue (fat) are first dissected by a dissecting device (dissector 3), and then a branch vessel exposed in the living body is stanched and cut by a cutting device (treatment sheath 2). Thus, the system of U.S. Pat. No. 7,981,127 is not configured in such a manner as to enable a blood vessel to be harvested together with the surrounding tissue. In addition, this system has a drawback in that the stanching and cutting may be conducted by capturing the branch vessel exposed in the living body, and, therefore, workability in harvesting the blood vessel is poor.

SUMMARY

Thus, there is a need for a treating device by which a blood vessel can be harvested together with the surrounding tissue with good workability.

In accordance with an exemplary embodiment, a treatment device is disclosed, which includes: a dissecting section main body which is configured to dissect tissue in a living body when inserted into the living body along a blood vessel, and which has a slit permitting a branch vessel branched from the blood vessel to enter into the slit; a stanching section which is disposed at the slit and which presses and cauterizes the branch vessel introduced into the slit; and a cutting section which is disposed at the slit and which cuts the cauterized branch vessel.

According to the treatment device configured as above, it is possible, when the treatment device is inserted into the living body along the blood vessel and moved forward, to dissect the tissue in the living body and to easily capture branch vessels embedded in the tissue, by the dissecting section main body. In addition, since the branch vessel introduced into the slit through the dissecting section main body is cauterized while pressed by the stanching section, even thin branch vessels can be stanched reliably. Further, since the cauterized branch vessel is cut by the cutting section, the stanched branch vessel can be cut reliably.

In the treatment device as above, at least a part of the stanching section may be configured such as to be displaceable in a separating direction of a first inner surface and a second inner surface which are opposed to each other and define the slit.

This configuration makes it possible to effectively press the branch vessel introduced into the slit, regardless of the thickness (diametric size) of the branch vessel.

In the treatment device as above, the stanching section may have a form of a leaf spring.

When this configuration is adopted, the leaf spring-like stanching section is elastically deformed attendant on the introduction of the branch vessel into the slit. Accordingly, the branch vessel can be pressed with an appropriate pressing force.

In the treatment device as above, the stanching section may include a stationary section fixed to one of the first inner surface and the second inner surface, and a pressing section which constitutes a free end on a proximal side of the stationary section and which presses the blood vessel. In accordance with an exemplary embodiment, this configuration can help enable the pressing section to be displaced with the stationary section as a center for displacement. Therefore, the branch vessel can be suitably pressed by the pressing section.

In the treatment device as above, the stanching section may have, between the stationary section and the pressing section, an inclined portion inclined toward one of the first inner surface and the second inner surface. In accordance with an exemplary embodiment, this configuration can help enable the branch vessel to be smoothly introduced to the pressing section under a guiding action of the inclined section.

In the treatment device as above, the stanching section may include a first electrode and a second electrode, which constitute bipolar electrodes.

Where this configuration is adopted, the branch vessel can be cauterized reliably by passing an electric current to that portion of the branch vessel which is located between the first electrode and the second electrode.

In the treatment device as above, the first electrode and the second electrode may be juxtaposed while spaced apart in a direction perpendicular to an axial direction of the treatment device.

Where this configuration is adopted, the branch vessel introduced into the slit in the state of extending in a direction intersecting the extending direction of the slit can be reliably supplied with an electric current and thereby cauterized.

In the treatment device as above, the first electrode and the second electrode may be fixed to the same side of the first inner surface and the second inner surface. In accordance with an exemplary embodiment, this configuration can help ensure that the branch vessel can be suitably pressed, by the first electrode and the second electrode, against the inner surface opposed to the inner surface onto which the first electrode and the second electrode are fixed.

In the treatment device as above, the cutting section may be projectingly provided at the stanching section. In accordance with an exemplary embodiment, this configuration can help enable the branch vessel stanched by the stanching section to be suitably cut.

The treatment device as above may further include a pressing member which is displaceably disposed in the slit and which, attendant on displacement thereof, presses the stanching section in a direction for the stanching section to press the branch vessel.

Where this configuration is adopted, the stanching section in the state of pressing the branch vessel is pressed by the pressing member, whereby the branch vessel can be sufficiently pressed flat in a radial direction. Then, by cauterizing the sufficiently pressed flat branch vessel, the branch vessel can be stanched reliably.

In the treatment device as above, the cutting section may be provided in the pressing member and be displaced together with the pressing member when the pressing member is displaced.

Where this configuration is adopted, it is unnecessary to displace the pressing section and the cutting section by individual operations. Therefore, the pressing of the stanching section by the pressing member and the cutting of the branch vessel by the cutting section can be easily carried out by a series of operations.

In the treatment device as above, the cutting section may be formed integral with the stanching section. This configuration can help enable a reduction in the number of component parts constituting the cutting section and the stanching section.

In the treatment device as above, the dissecting section main body may be provided at its distal portion with an introducing section which communicates with the slit and the opening width of which decreases in the proximal direction. This configuration can help enable smooth guiding of the branch vessel into the slit.

In the treatment device as above, the slit may include a first slit element along the thickness direction of the dissecting section main body, and a second slit element intersecting the first slit element.

Where this configuration is adopted, a dissecting section main body formed with the slit for introducing the branch vessel can be easily constructed, for example, by a method wherein a first member and a second member one of which is formed with a slit-shaped groove are laid over each other and joined to each other.

In another aspect, there is provided a dissecting device including: a grasping section which has an insertion lumen permitting an imaging device to be inserted therein and which is adapted to be graspable by a user; and a dissecting member which is provided at a distal portion of the grasping section and which, when inserted into a living body along a blood vessel, dissects tissue in the living body, wherein the dissecting member includes a first dissecting section, and a second dissecting section extending from the first dissecting section in a thickness direction of the first dissecting section, and the second dissecting section is composed of the above-mentioned treatment device.

In accordance with another aspect, a method is disclosed for dissecting tissue, the method comprising: introducing a dissecting device having a dissecting section main body which is configured to dissect tissue into a living body along a blood vessel, the dissecting device having a slit, which permits a branch vessel branched from the blood vessel to enter into the slit; cauterizing the branch vessel introduced into the slit in a stanching section which is disposed at the slit, and wherein at least a part of the stanching section is configured to be displaceable in a separating direction of a first inner surface and a second inner surface which are opposed to each other and define the slit; and cutting the cauterized branch vessel with a cutting section which is disposed at the slit.

In accordance with the treatment device and the dissecting device of the described aspects of the present disclosure, a blood vessel can be harvested together with the surrounding tissue, while easily capturing branch vessels embedded in the tissue and easily stanching and cutting the branch vessels. Thus, excellent workability can be ensured.

BRIEF DESCRIPTION OF THE DRAWINGS

FIG. 20 is a fourth illustration for explaining a treatment of a branch vessel by a side section according to a third modification.

DETAILED DESCRIPTION OF THE PREFERRED EMBODIMENTS

The treatment device according to the present disclosure will be described below by showing preferred embodiments thereof while referring to the attached drawings.

Figure 1:
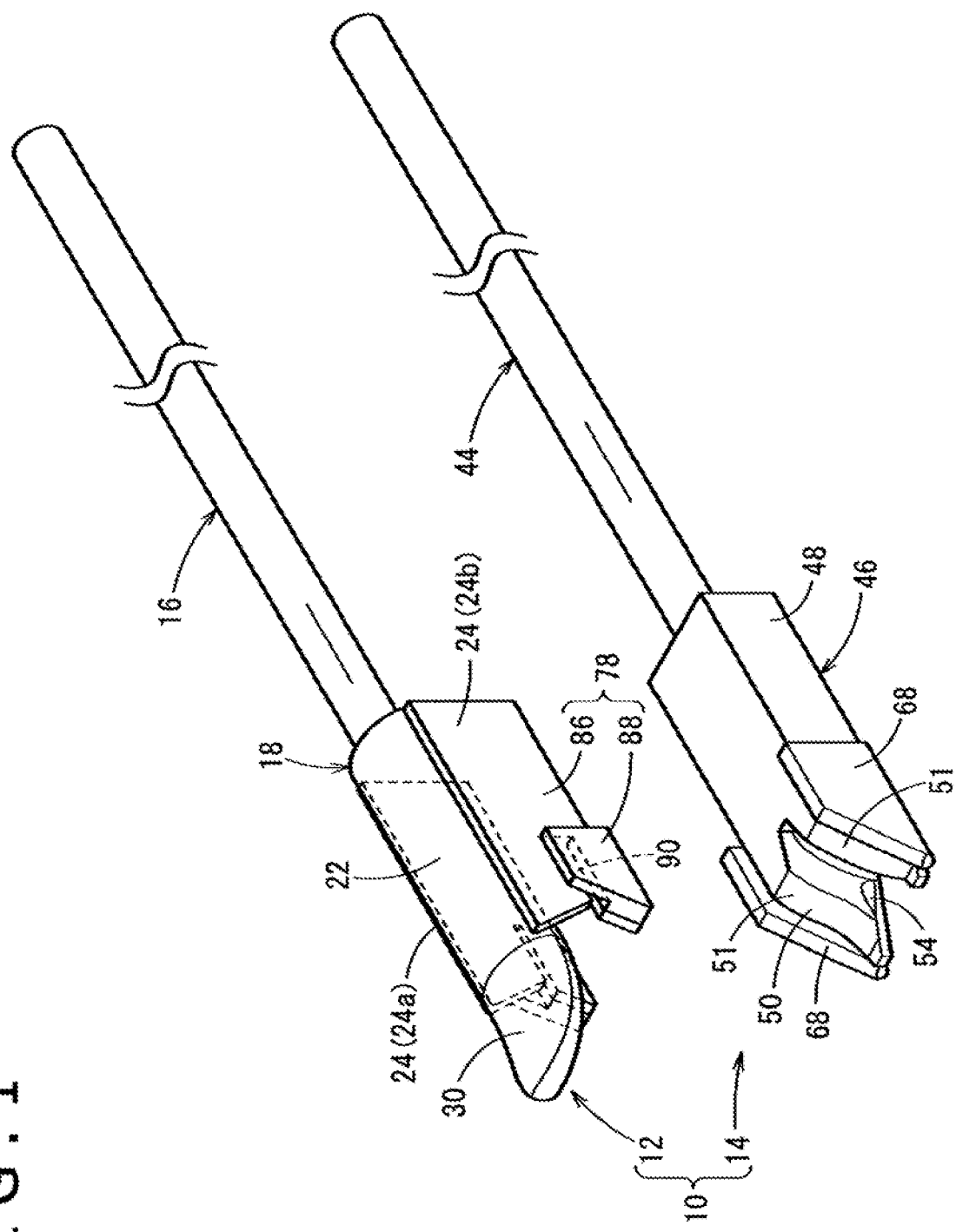
FIG. 1 is a perspective view of a dissecting system in accordance with an exemplary embodiment.

A dissecting system 10 shown in FIG. 1 is a device used to harvest a blood vessel for use as a bypass vessel in carrying out blood vessel bypass grafting (particularly, coronary artery bypass grafting: CABG). By use of the dissecting system 10, a blood vessel can be harvested in the state of being covered with the surrounding tissue (fat, connective tissue, etc.). The blood vessel to be harvested using the dissecting system 10 is not particularly limited so long as it is a blood vessel that can be used as a bypass vessel. Examples of the applicable blood vessel include internal thoracic artery, gastroepiploic artery, radial artery, and saphenous veins (great saphenous vein and small saphenous vein).

It can be preferable, however, that the blood vessel to be harvested is a saphenous vein. The use of the dissecting system 10 can facilitate harvesting of a blood vessel in the state of being covered with the surrounding tissue, as aforementioned. It is considered, therefore, that when a saphenous vein is harvested by use of the dissecting system 10 and is used as a bypass vessel, an enhanced long-term patency rate can be obtained after the bypass grafting.

In accordance with an exemplary embodiment, the dissecting system 10 can include two dissecting devices 12 and 14. Hereinafter, one 12 of the two dissecting devices 12 and 14 will be referred to as "the first dissecting device 12," and the other 14 as "the second dissecting device 14." Both the first dissecting device 12 and the second dissecting device 14 are each an elongated device to be inserted into a living body along a blood vessel such as a saphenous vein.

Figure 3:
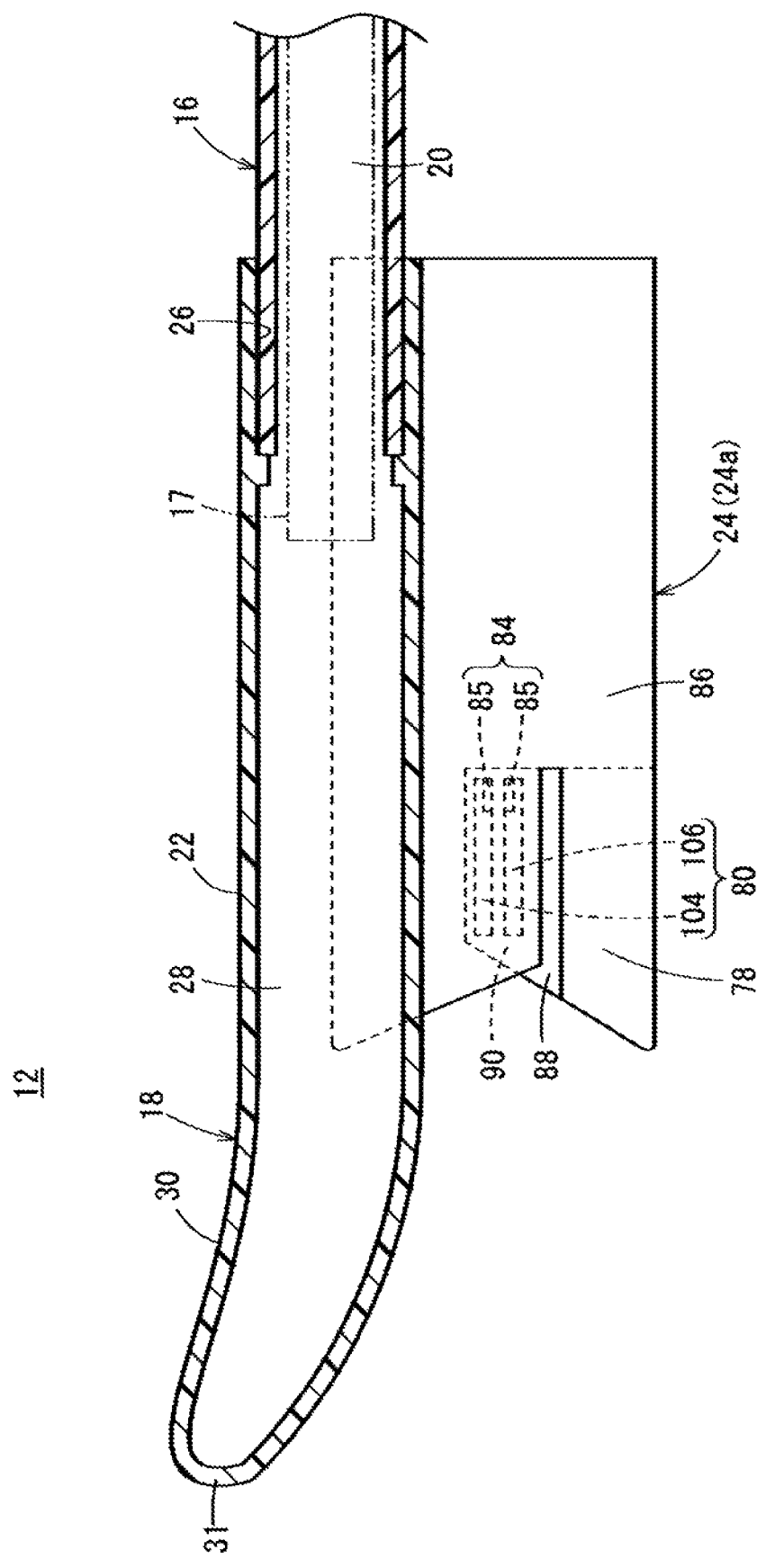
FIG. 3 is a sectional view of a distal portion of the first dissecting device.

The first dissecting device 12 can include a grasping section 16 adapted to be graspable by a user (technician), and a dissecting member 18 provided at a distal portion of the grasping section 16. As depicted in FIG. 3, the grasping section 16 is a tubular member having an insertion lumen 20 in which an imaging device 17 (for example, an endoscope) can be inserted. The grasping section 16 in the illustrated example is formed in a rectilinear shape. Examples of the material constituting the grasping section 16 can include rigid resins and metals.

The insertion lumen 20 is a through-hole which extends along a longitudinal direction of the grasping section 16 and which opens at a distal surface and a proximal surface of the grasping section 16. At a distal portion of the imaging device 17, an objective lens and an illuminating portion can be provided, for example.

In FIG. 1, the dissecting member 18 can include a hollow-structured base section 22 (first dissecting section) which is fixed to a distal portion of the grasping section 16, and a pair of side sections 24 (second dissecting section) projecting from both sides with respect to a width direction of the base section 22 toward one side (lower side in FIG. 1) with respect to a thickness direction of the base section 22. The base section 22 has a flattened cross-sectional shape, which is short in the vertical direction and long in the width direction. In accordance with an exemplary embodiment, the width of the base section 22 is set to be greater than the outside diameter of a blood vessel to be harvested.

In FIG. 3, the base section 22 can include a fixing hole 26 in which a distal portion of the grasping section 16 is fixed, and a cavity 28, which extends from a position slightly distal of the fixing hole 26 to the vicinity of a distal end of the base section 22. The cavity 28 communicates with the insertion lumen 20.

The base section 22 is provided at its distal portion with a distal dissecting section 30, which dissects tissue. The distal dissecting section 30 is tapered distally, for easy dissection of tissue. Specifically, the distal dissecting section 30 is formed in such a shape that the length in a minor axis direction and the length in a major axis direction of its cross-sectional shape gradually decrease in the distal direction. A distal end 31 (apex portion) of the distal dissecting section 30 can be formed in a rounded shape, in order to help prevent the distal dissecting section 30 from damaging a blood vessel to be harvested or branch vessels 73. In addition, the distal dissecting section 30 can be curved in the manner of gradually warping upward from a base portion located on the proximal side thereof.

In accordance with an exemplary embodiment, the base section 22 is formed of a transparent (light-transmitting) material (for example, glass, or transparent resin). With the imaging device 17 inserted in the insertion lumen 20 and the cavity 28, therefore, the front side and the surroundings of the base section 22 can be imaged for observation (visual confirmation) by the imaging device 17. Note that it is preferable that the base section 22 is substantially colorless and transparent, but the base section 22 may be colored so long as it is transparent.

Figure 8:
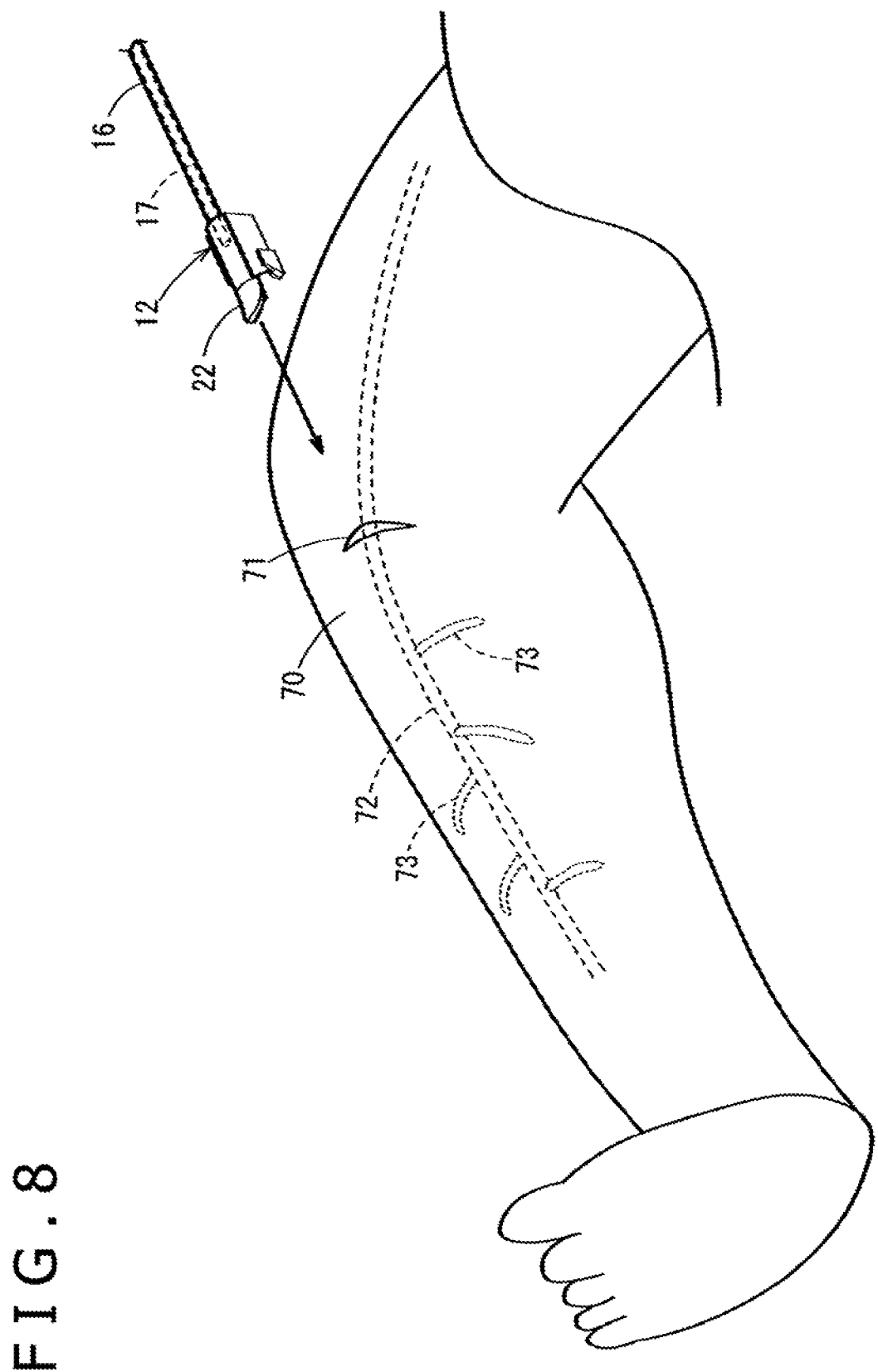
FIG. 8 illustrates a method of inserting the first dissecting device into a living body.

In FIG. 1, the pair of side sections 24 (24a and 24b) is configured such that they dissect tissue on both lateral sides under the base section 22 and they are able to stanch and cut the branch vessels 73 (see FIG. 8). The pair of side sections 24 are configured in left-right symmetry (symmetry with respect to the width direction of the dissecting member 18).

The pair of side sections 24 are provided at near-proximal-end portions on both lateral sides of the base section 22. Therefore, the base section 22 having the distal dissecting section 30 protrudes distally beyond the pair of side sections 24. In this embodiment, the base section 22 and the pair of side sections 24 are formed integrally. Note that the base section 22 and the pair of side sections 24 may be configured as separate members and be joined to one another by appropriate means (for example, an adhesive).

Figure 2:
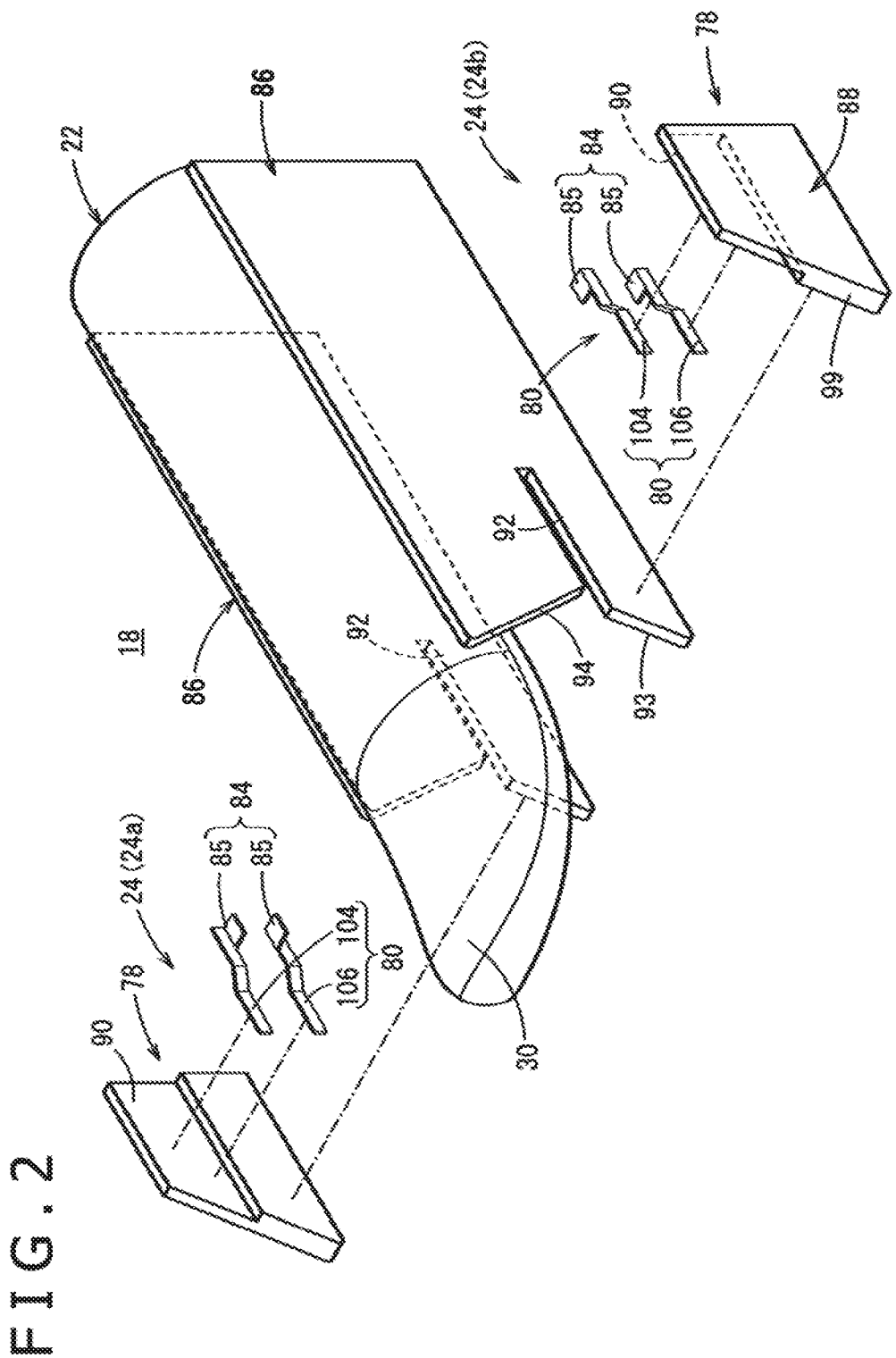
FIG. 2 is an exploded perspective view of a dissecting member of a first dissecting device.
Figure 4:
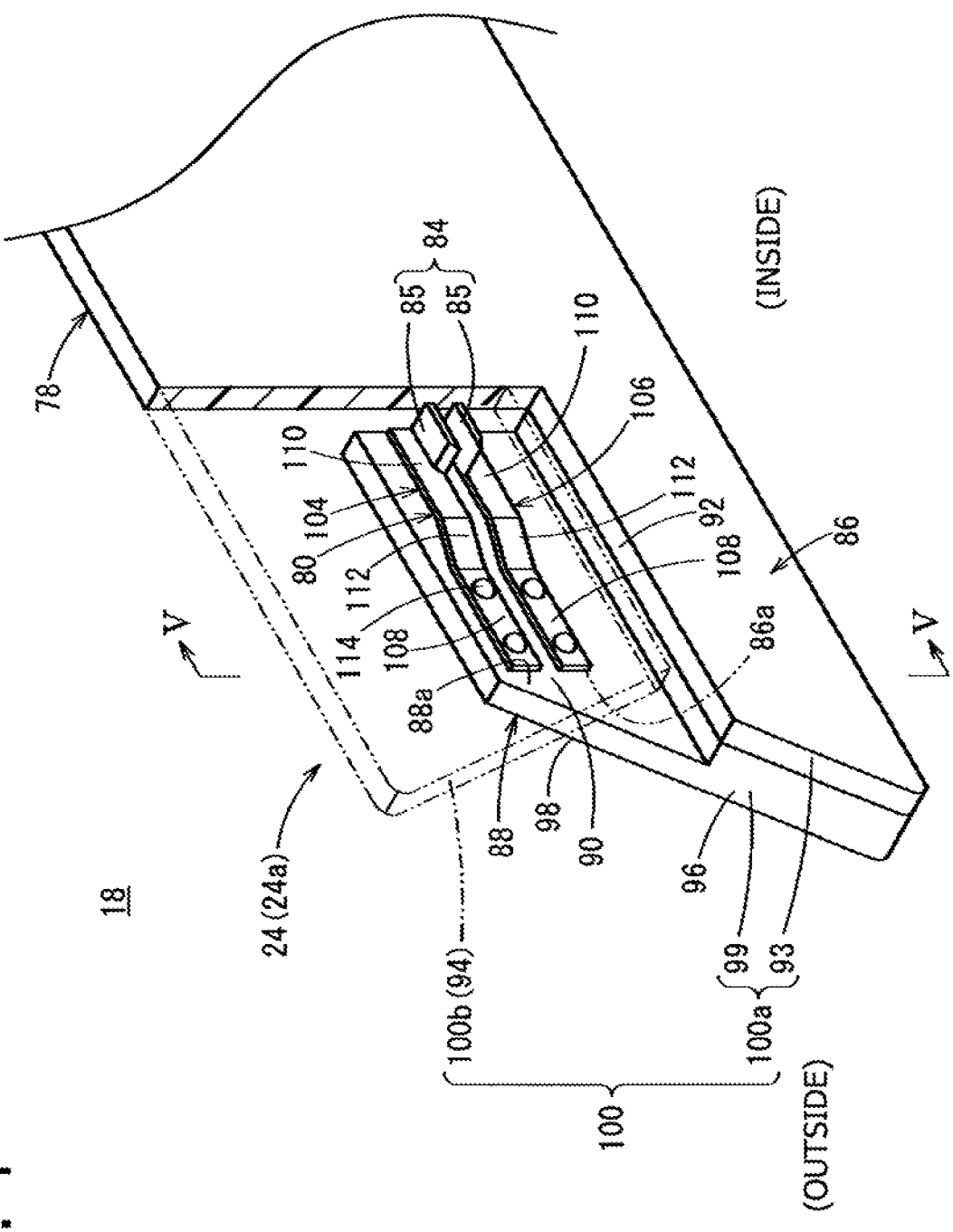
FIG. 4 is a perspective view of a side section of the first dissecting device.

In FIGS. 2 and 4, the side section 24 can include a dissecting section main body 78 having a slit 90 into which the branch vessel 73 can enter, a stanching section 80 for stanching the branch vessel 73, and a cutting section 84 for cutting the branch vessel 73. Note that in FIG. 4, a part of the dissecting section main body 78 (a part of a first member 86 to be described later) is indicated by an imaginary line, for ease of understanding.

The dissecting section main body 78 is configured to dissect tissue in a living body when inserted into the living body along a blood vessel, and can include the first member 86 and a second member 88. The first member 86 and the second member 88 are formed in a plate-like shape. The slit 90 is formed between the first member 86 and the second member 88. The first member 86 and the second member 88 are formed of a transparent material, like the base section 22.

In this embodiment, the first member 86 is a plate-shaped body which constitutes a main body portion of the side section 24, and which projects from the base section 22 toward one side with respect to the thickness direction of the base section 22. The first member 86 has a slit-shaped groove 92 extending in the longitudinal direction of the dissecting member 18 (the axial direction of the grasping section 16). The slit-shaped groove 92 penetrates the first member 86 in the thickness direction of the first member 86 and opens in the distal direction. In addition, at a distal portion of the first member 86, there are formed inclined surfaces 93 and 94, which are inclined in such a manner as to approach the slit-shaped groove 92 proximally.

As depicted in FIG. 4, the second member 88 is a plate-shaped body joined to the first member 86. The first member 86 and the second member 88 are joined together in the thickness direction thereof. In this embodiment, the second member 88 is disposed on the outside of the first member 86.

In this embodiment, the second member 88 can include a thick portion 96 and a thin portion 98 projecting from the thick portion 96. The thick portion 96 is joined to one of two portions of the first member 86, which are on opposite sides of the slit 90. The thin portion 98 faces the other of the two portions of the first member 86 which are on opposite sides of the slit 90, with a gap between the thin portion 98 and the other of the two portions of the first member 86. Thus, in this embodiment, the slit-shaped groove 92 formed in the first member 86 and the gap between the first member 86 and the second member 88 form the slit 90.

Figure 5:
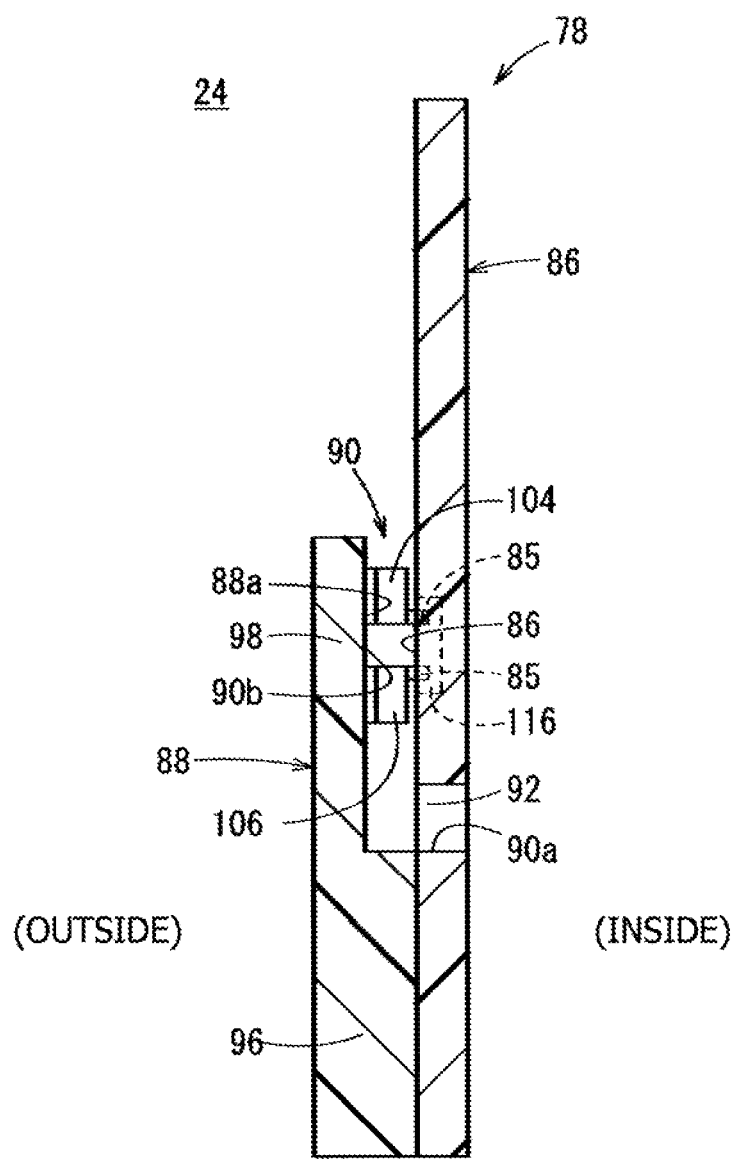
FIG. 5 is a sectional view of the side section, taken along line V-V of FIG. 4.

In accordance with an exemplary embodiment, the slit 90 as above is crooked in an L shape in a cross section of the dissecting section main body 78, as depicted in FIG. 5. Specifically, for example, the slit 90 can include a first slit element 90a along the thickness direction of the dissecting section main body 78, and a second slit element 90b along a direction orthogonal to the first slit element 90a (a direction intersecting the first slit element 90a). Therefore, the slit 90 can open to one side with respect to the thickness direction of the dissecting section main body 78 (to the inside of the dissecting member 18) and to one side with respect to a direction which is orthogonal to the longitudinal direction of the dissecting member 18 and the thickness direction of the dissecting section main body 78 (to the side of a projecting end of the thin portion 98). In addition, as shown in FIG. 4, the slit 90 can open also to the distal side and to the proximal side.

In FIG. 4, at a distal portion of the second member 88, there is formed an inclined surface 99 inclined in such a manner as to approach the projecting end of the thin portion 98 proximally.

At a distal portion of the dissecting section main body 78, an introducing section 100 is formed, which has an opening width decreasing in the proximal direction and which communicates with the slit 90. Specifically, this introducing section 100 is composed of a first inclined end edge 100a and a second inclined end edge 100b. The first inclined end edge 100a is composed of the inclined surface 93 on one side of the first member 86 mentioned above and the inclined surface 99 of the second member 88. The second inclined end edge 100b is composed of the inclined surface 94 on the other side of the first member 86 mentioned above.

The stanching section 80 is configured to press and stanch the branch vessel 73 introduced into the slit 90. The stanching section 80 can include a first electrode 104 and a second electrode 106 which constitute bipolar electrodes. The first electrode 104 and the second electrode 106 are juxtaposed while spaced apart from each other in a direction perpendicular to the extending direction of the dissecting member 18 (specifically, in the height direction of the dissecting member 18, in other words, in the width direction of the dissecting section main body 78). In addition, the first electrode 104 and the second electrode 106 are disposed along the extending direction of the slit 90 in parallel to each other. Energization of (impressing of a high-frequency voltage on) the bipolar electrodes is configured in such a manner that the first electrode 104 and the second electrode 106 can be energized simultaneously or that the first electrode 104 and the second electrode 106 can be energized selectively, through an interface provided on the user's hand side.

With a high-frequency voltage impressed between the first electrode 104 and the second electrode 106 configured as above, the branch vessel 73 introduced into the slit 90 can be stanched through cauterization (thermal coagulation). Note that the user performs an energizing operation on the user's hand side of the first dissecting device 12 to effect an energy-outputting operation, whereby a high-frequency voltage is impressed between the first electrode 104 and the second electrode 106.

In accordance with an exemplary embodiment, the dissecting section main body 78 has a first inner surface 86a and a second inner surface 88a which are opposed to each other and define the slit 90. The first inner surface 86a is formed in the first member 86. The second inner surface 88a is formed in the second member 88. The first electrode 104 and the second electrode 106 can be fixed to one of the first inner surface 86a and the second inner surface 88a (in this embodiment, the second inner surface 88a).

At least a part of the stanching section 80 is configured to be displaceable in the separating direction (hereinafter referred to as "the slit thickness direction") of the first inner surface 86a and the second inner surface 88a which are on opposite sides of the slit 90. Specifically, for example, the first electrode 104 and the second electrode 106 each can have a form of a leaf spring (elastic piece).

Figure 6A:
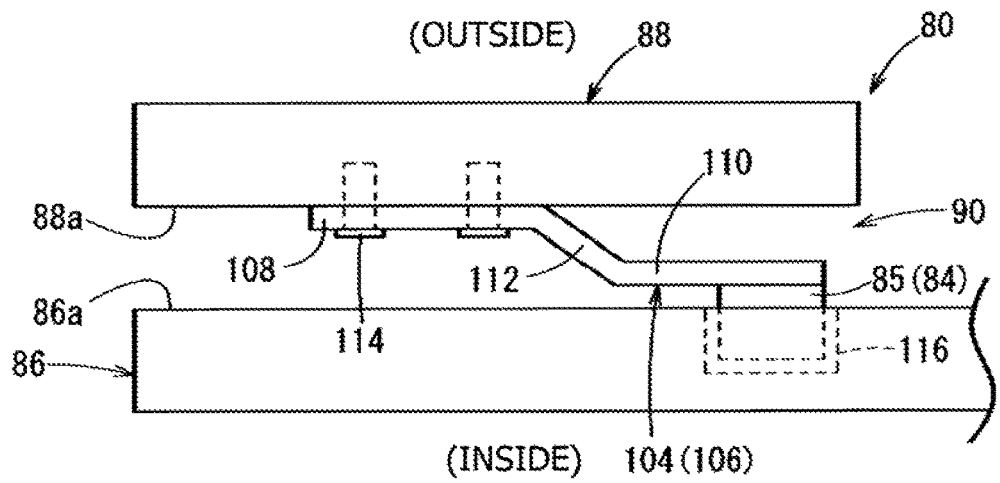
FIG. 6A is a schematic plan view of the side section.

In FIGS. 4 and 6A, each of the first electrode 104 and the second electrode 106 can include a stationary section 108 fixed to one of the first inner surface 86a and the second inner surface 88a (in this embodiment, the second inner surface 88a), and a pressing section 110 which presses the branch vessel 73 on the proximal side of the stationary section 108. The stationary section 108 constitutes a distal-side region of each of the first electrode 104 and the second electrode 106, and is attached to the second member 88 by appropriate fixing means (joining means) 114.

The pressing section 110 is configured such that it can be elastically displaced in the slit thickness direction and that it presses the branch vessel 73 introduced into the slit 90 toward the other of the first inner surface 86a and the second inner surface 88a (in this embodiment, the first inner surface 86a). The pressing section 110 constitutes a proximal-side region of each of the first member 86 and the second member 88, and constitutes a free end portion. The pressing section 110 may be in contact with the other of the first inner surface 86a and the second inner surface 88a. In that case, the pressing section 110 may bias the other of the first inner surface 86a and the second inner surface 88a. Alternatively, the pressing section 110 may only make contact with, and may not bias, the other of the first inner surface 86a and the second inner surface 88a. Such a configuration helps ensure that the pressing section 110 can reliably make contact with the branch vessel 73.

Each of the first electrode 104 and the second electrode 106 further can include an inclined section 112 constituting a portion between the stationary section 108 and the pressing section 110. The inclined section 112 is inclined such as to approach the first inner surface 86a proximally. The inclined section 112 may be curved or rectilinear in shape.

Note that the second member 88 may be disposed on the inside of the first member 86. The first electrode 104 and the second electrode 106 may be fixed to the first inner surface 86a. A configuration may be adopted wherein one of the first electrode 104 and the second electrode 106 is fixed to one of the first inner surface 86a and the second inner surface 88a whereas the other of the first electrode 104 and the second electrode 106 is fixed to the other of the first inner surface 86a and the second inner surface 88a.

The cutting section 84 has a sharp cutting edge, and is configured to cut the branch vessel 73 having undergone the stanching (thermal coagulation) by the stanching section 80. The cutting section 84 is provided at a proximal portion of the stanching section 80 (specifically, for example, at a proximal portion of the pressing section 110), which helps ensure that the branch vessel 73 introduced into the slit 90 is cauterized while pressed by the pressing section 110, thereby being stanched, and then reaches the cutting section 84, by which the stanched portion (cauterized portion) is cut. In addition, the cutting section 84 may be integral with the pressing section 110. This configuration helps ensure that since the cutting section 84 is composed of the first electrode 104 and the second electrode 106, the stanched portion (cauterized portion) of the branch vessel 73 can be cut by burning by the cutting section 84. In addition, for easy cutting of the branch vessel 73, components of the cutting section 84 may each project from the first electrode 104 and the second electrode 106 toward the side of that one of the first inner surface 86a and the second inner surface 88a onto which the first electrode 104 and the second electrode 106 are not fixed (in this embodiment, the side of the first inner surface 86a).

As illustrated in FIG. 4, the cutting section 84 has two cutter pieces 85. One of the cutter pieces 85 is provided in the first electrode 104, while the other of the cutter pieces 85 is provided in the second electrode 106. The two cutter pieces 85 project respectively from the first electrode 104 and the second electrode 106 toward the side of that one of the first inner surface 86a and the second inner surface 88a onto which the first electrode 104 and the second electrode 106 are not fixed (in this embodiment, the side of the first inner surface 86a).

The two cutter pieces 85 are each formed integral with the first electrode 104 and the second electrode 106. Specifically, for example, one of the cutter pieces 85 is one member formed integral with the first electrode 104. Similarly, the other of the cutter pieces 85 is one member formed integral with the second electrode 106. Note that the two cutter pieces 85 may be separate members that are joined individually to the first electrode 104 and the second electrode 106. The cutting section 84 may have only one of the cutter pieces 85 (for example, may lack one of the two cutter pieces 85).

In FIG. 6A, that one of the first inner surface 86a and the second inner surface 88a onto which the stanching section 80 is not fixed (the first inner surface 86a) is provided with an accommodation groove 116 in which the cutting section 84 is accommodated. Where such an accommodation groove 116 is provided, interference between the first inner surface 86a and the cutting section 84 can be prevented, and the branch vessel 73 introduced into the slit 90 can be reliably pressed by the pressing section 110.

Figure 7:
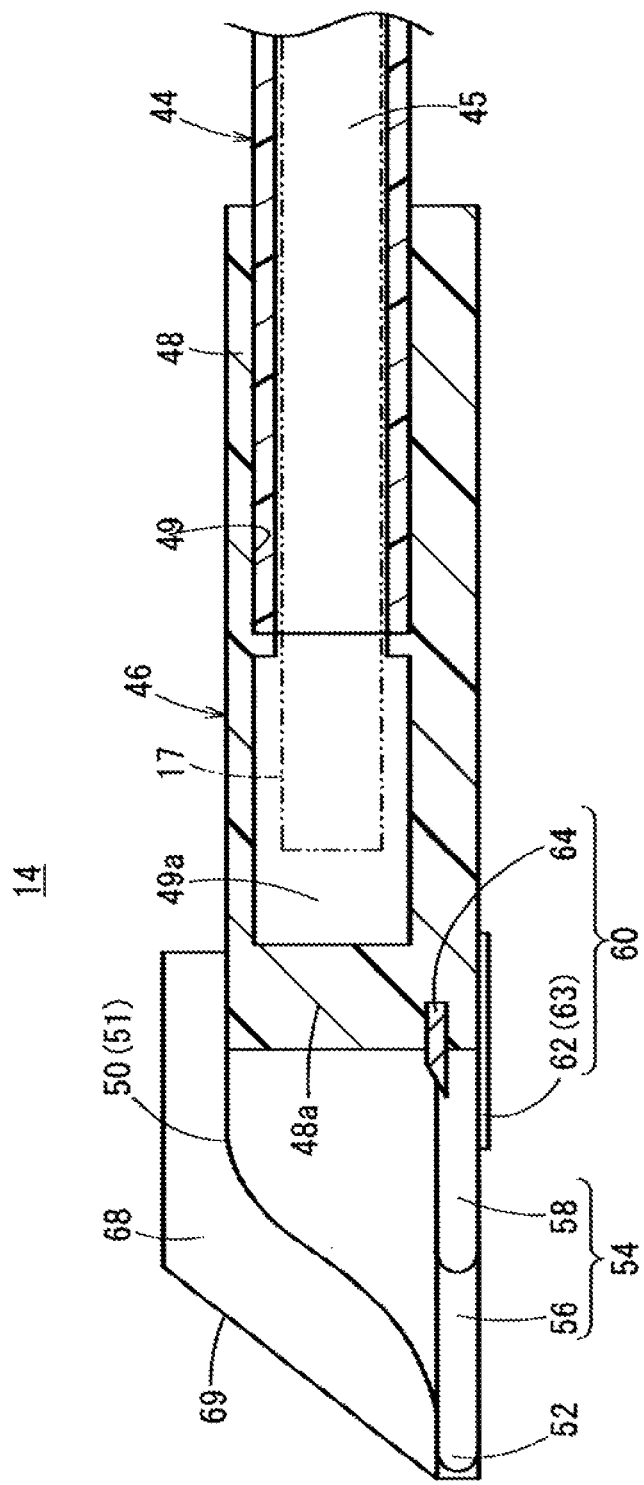
FIG. 7 is a sectional view of a distal portion of a second dissecting device.

In FIG. 1, the second dissecting device 14 can include a grasping section 44 adapted to be graspable by the user, and a dissecting member 46 provided at a distal portion of the grasping section 44. As depicted in FIG. 7, the grasping section 44 is a tubular member having an insertion lumen 45 in which an imaging device 17 can be inserted. The grasping section 44 in the illustrated example is formed in a rectilinear shape. Examples of the material constituting the grasping section 44 can include rigid resins and metals. The insertion lumen 45 is a through-hole which extends along a longitudinal direction of the grasping section 44 and which opens at a distal surface and a proximal surface of the grasping section 44.

The dissecting member 46 can include a base part 48 fixed to a distal portion of the grasping section 44, and a dissecting section 50 extending distally from a distal end of the base part 48. The base part 48 is formed in a hollow shape having a lumen 49, which extends along a longitudinal direction of the dissecting member 46. A distal end of the lumen 49 is closed by a distal end wall 48a of the base part 48. A proximal end of the lumen 49 is opening at a proximal end surface of the base part 48. A distal portion of the grasping section 44 is inserted and fixed in a proximal-side region of the lumen 49. The lumen 49 is provided, on the distal side of the grasping section 44, with a cavity 49a into which a distal portion of the imaging device 17 can enter.

The base part 48 in the illustrated example has a cross-sectional profile which is tetragonal in shape. Note that the cross-sectional profile of the base part 48 may be other shape than a tetragon, for example, such as a circle, an ellipse, or a trapezoid.

The dissecting member 46 (particularly, the base part 48) is transparent (light-transmitting). Examples of the material constituting the dissecting member 46 can include glass and transparent resin. With the base part 48 thus transparent, when the imaging device 17 is inserted in the insertion lumen 45, the front side and the surroundings of the base part 48 can be imaged for observation by the imaging device 17.

Note that although it is preferable that the dissecting member 46 is substantially colorless and transparent, the dissecting member 46 may be colored so long as it is transparent. The dissecting member 46 may not necessarily be entirely transparent, and only the base part 48 (particularly, only the distal end wall 48a functioning as an observation window) may be transparent. In addition, in the dissecting member 46, the distal end wall 48a may not necessarily be a portion formed integral with other portion; thus, a distal end opening of the cavity 49a may be closed with a separate transparent member.

As illustrated in FIG. 1, the dissecting section 50 can include a pair of dissecting portions 51 which dissect tissue (for example, fat 74) when the dissecting member 46 is moved forward along a blood vessel 72. The pair of dissecting portions 51 are spaced apart in the width direction of the dissecting member 46. In order that tissue is easily dissected in the direction of alignment of the blood vessel 72 with the dissecting member 46, the thickness (the dimension measured in the height direction of the dissecting member 46) of each dissecting portion 51 gradually increases in the proximal direction.

The dissecting member 46 is further provided at its distal portion with a blood vessel guide passage 54 by which a branch vessel 73 is accepted and is guided toward the base part 48 side. The blood vessel guide passage 54 is formed between the above-mentioned pair of dissecting portions 51. As depicted in FIG. 7, the blood vessel guide passage 54 can include a first groove section 56 (introducing section 100) constituting a distal-side region of the blood vessel guide passage 54, and a second groove section 58 constituting a proximal-side region of the blood vessel guide passage 54.

The first groove section 56 is formed to have a width, which decreases in the proximal direction. The second groove section 58 is a rectilinear groove, which communicates with the first groove section 56, is smaller than the first groove section 56 in width, and extends along the longitudinal direction of the dissecting member 46.

In addition, the dissecting member 46 is provided with a treating section 60 for stanching and cutting the branch vessel 73. The treating section 60 can include a stanching section 62 for stanching the branch vessel 73, and a cutting section 64 (cutting edge section) for cutting the branch vessel 73. The stanching section 62 has a bipolar structure including a pair of electrodes 63. The pair of electrodes 63 are provided respectively on both sides with respect to the width direction of the second groove section 58. In the illustrated example, the pair of electrodes 63 are attached to a bottom surface of the dissecting member 46. Note that the pair of electrodes 63 may be disposed in the manner of being embedded in the dissecting member 46.

Application of a high-frequency voltage between the pair of electrodes 63 thus configured permits the branch vessel 73 guided into the second groove section 58 to be stanched by cauterization (thermal coagulation). The cutting section 64 is provided at a deepest part (proximal part) of the second groove section 58, and is provided on the proximal side of the distal ends of the pair of electrodes 63, which helps ensure that the cauterized branch vessel 73 can be cut by the cutting section 64.

In addition, the treating section 60 may have a bipolar structure including the electrodes 63 as one-side electrodes (hereinafter referred to as "the first electrodes 63") and the cutting section 64 as the other-side electrode (hereinafter referred to as "the second electrode 64"). The second electrode 64 is a cutting edge portion or has a sheet structure, and also has a cutting function of cutting the cauterized branch vessel 73. The first electrodes 63 are provided on both sides with respect to the width direction of the second groove section 58 to the proximal portion side. In FIG. 7, the first electrodes 63 are attached to a bottom surface of the dissecting member 46. The first electrodes 63 may be disposed in the manner of being embedded in the dissecting member 46.

In FIG. 1, the dissecting member 46 further can include a pair of guide plates 68 formed on both lateral sides of the dissecting section 50. With such a pair of guide plates 68 provided, it can help ensure that when the second dissecting device 14 is pushed forward in the distal direction within a living body, the guide plates 68 are inserted into dissected parts precedingly formed by the side sections 24 of the dissecting member 18. Consequently, the second dissecting device 14 can be easily pushed forward along the blood vessel 72.

Now, a blood vessel harvesting method in which the dissecting system 10 configured as above is used will be described below. The blood vessel harvesting method can include a dissecting step (first step) of dissecting a blood vessel 72 in the state of being covered with surrounding fat 74 (tissue) by use of the dissecting system 10, a cutting step (second step) of cutting the blood vessel 72 ligated, and an extracting step (third step) of extracting the blood vessel 72 in the state of being covered with the surrounding fat 74 from the living body. Note that in this example, a case of harvesting a saphenous vein in a lower limb will be explained.

In the dissecting step, first, the position of the blood vessel 72 to be harvested is confirmed, and a patient's skin 70 is incised based on the position, as illustrated in FIG. 8, for example. After the skin 70 is incised, tissue is dissected until the blood vessel 72 appears (until the blood vessel 72 or a saphenous fascia is exposed). Next, the first dissecting device 12 with the imaging device 17 inserted therein is prepared. Note that the first dissecting device 12 may be preliminarily provided with the imaging device 17 as a component thereof.

Then, while observing the inside of the living body through the imaging device 17, the first dissecting device 12 is inserted into the living body along the blood vessel 72 via an incision 71. In this case, the first dissecting device 12 is inserted in such a manner that the base section 22 of the dissecting member 18 is disposed between the skin 70 and the blood vessel 72, and the thickness direction of the base section 22 coincides with the direction of alignment of the base section 22 with the blood vessel 72.

Figure 9:
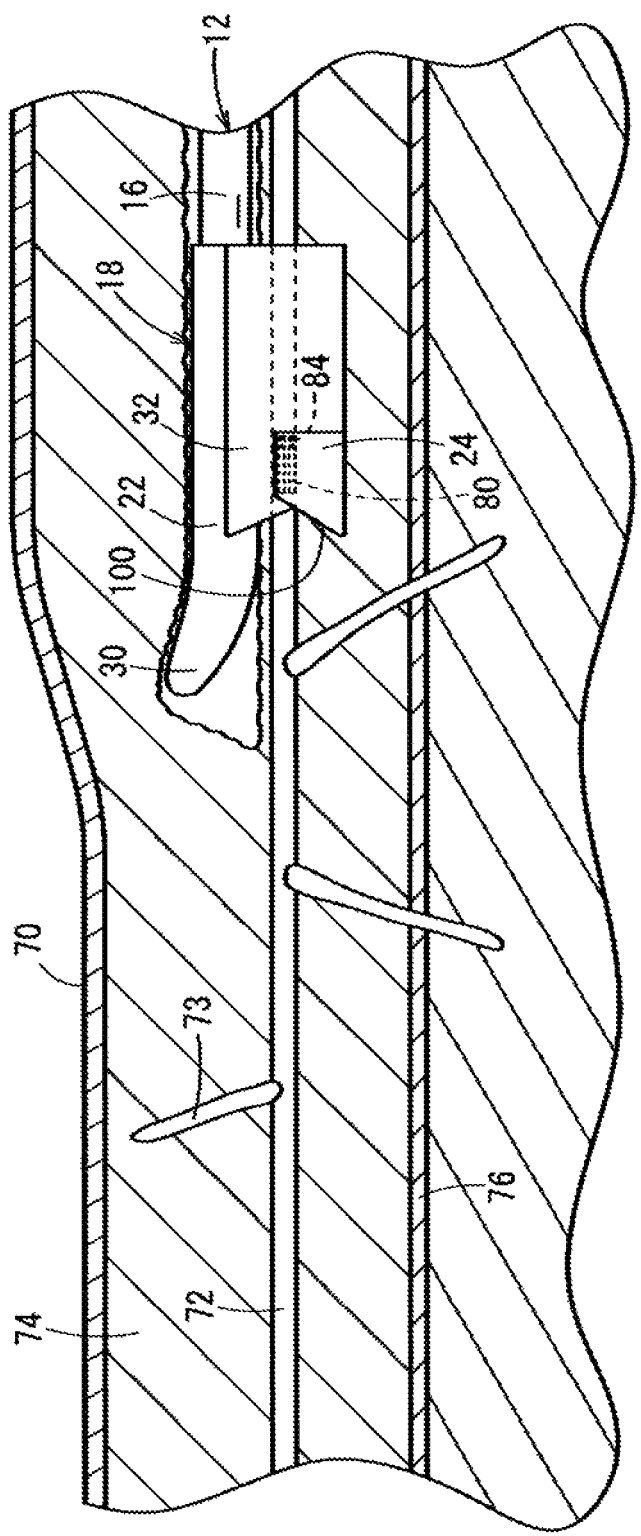
FIG. 9 is a sectional view along an extending direction of a blood vessel in a living body, for explaining a state in which the first dissecting device is moved forward in the living body along the blood vessel.
Figure 10:
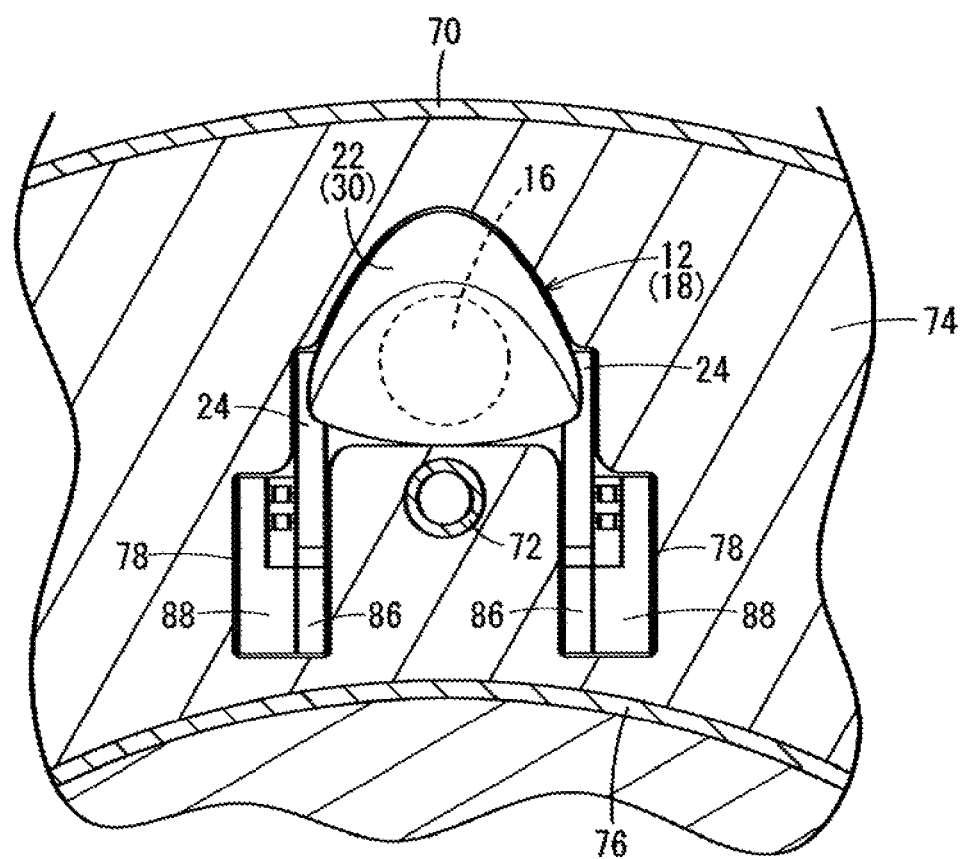
FIG. 10 is a sectional view in a direction perpendicular to the blood vessel in the living body, for explaining the state in which the first dissecting device is moved forward in the living body along the blood vessel.

Then, in the living body, the first dissecting device 12 is pushed forward along the blood vessel 72 by a distance corresponding to a required length (a length to be harvested). In this case, as illustrated in FIG. 9, the first dissecting device 12 is moved forward while dissecting the fat 74 surrounding the blood vessel 72 by the dissecting member 18. Specifically, for example, the distal dissecting section 30 of the base section 22 dissects the fat 74 present on the upper side (the skin 70 side) of the blood vessel 72 in the thickness direction of the base section 22. As shown in FIG. 10, the pair of side sections 24 dissect the fat 74 present on lateral sides of the blood vessel 72 in the thickness direction of the side sections 24.

Figure 11A:
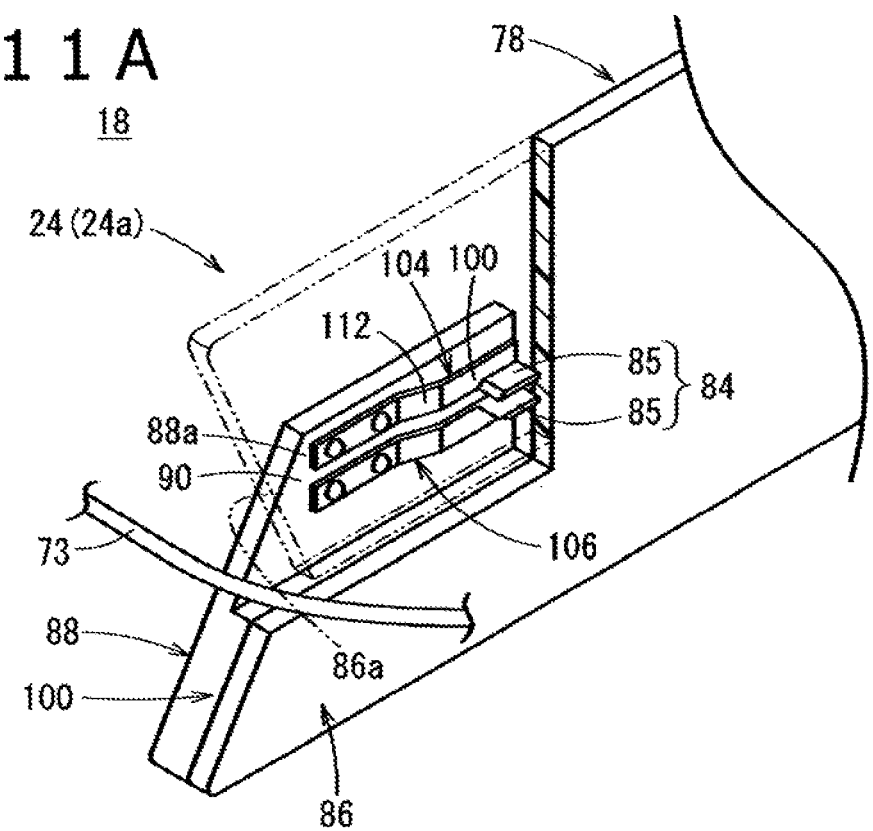
FIG. 11A is a first illustration for explaining a treatment of a branch vessel by the side section.

In addition, when the first dissecting device 12 is moved forward within the living body along the blood vessel 72, as shown in FIG. 9, the first dissecting device 12 guides the branch vessels 73 branched from the blood vessel 72 by the introducing section 100 into the slit 90, and stanches and cuts the branch vessels 73 by the stanching section 80 and the cutting section 84 provided at the slit 90. Specifically, for example, as illustrated in FIG. 11A, when the side sections 24 contact the branch vessel 73 in the process of forward movement of the first dissecting device 12 in the living body, the branch vessel 73 is smoothly guided into the slit 90 side under a guiding action of the introducing section 100 the opening width of which decreases in the proximal direction.

Figure 11B:
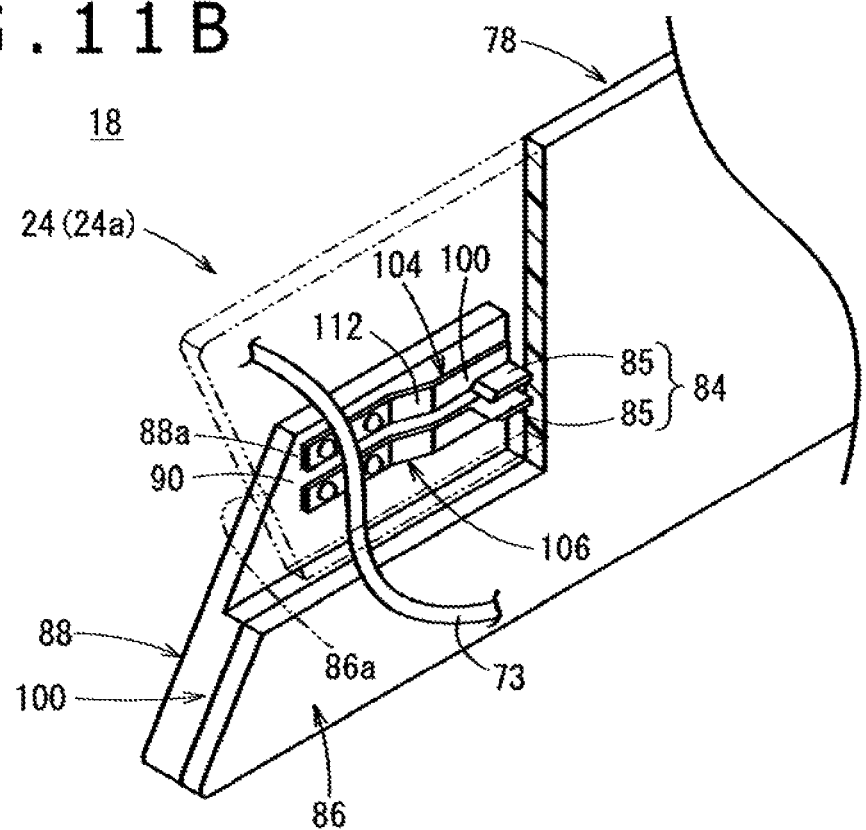
FIG. 11B is a second illustration for explaining the treatment of the branch vessel by the side section.
Figure 12A:
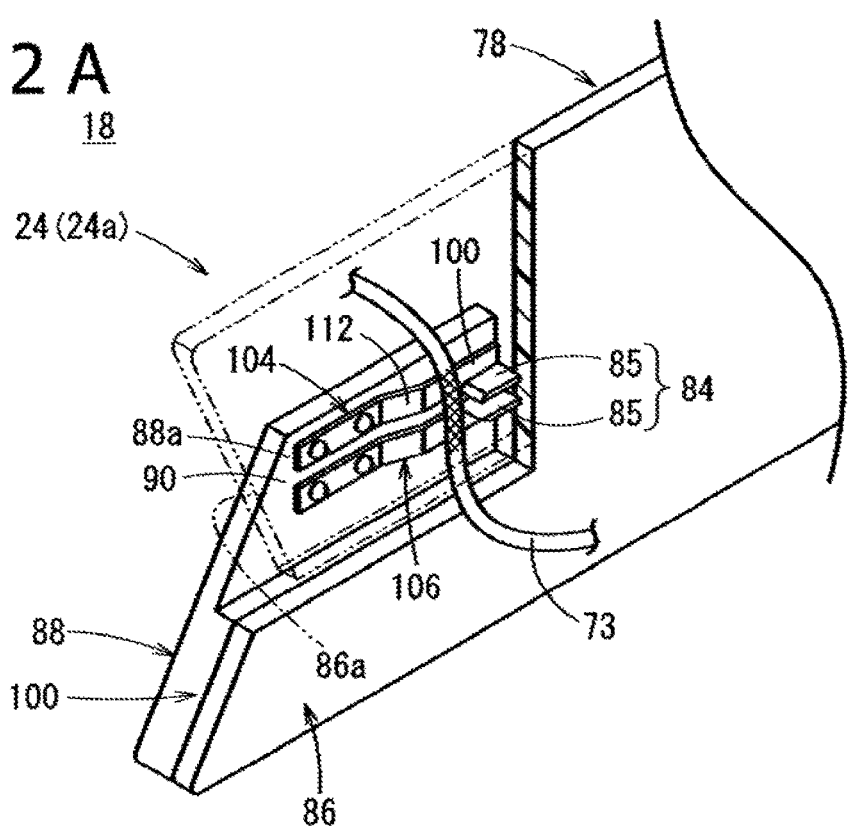
FIG. 12A is a third illustration for explaining the treatment of the branch vessel by the side section.

Then, attendant on a further forward movement of the first dissecting device 12, the branch vessel 73 is introduced into the slit 90, as depicted in FIG. 11B. When the first dissecting device 12 is further moved forward, the branch vessel 73 reaches the pressing sections 110 of the first electrode 104 and the second electrode 106 by way of the inclined sections 112, as illustrated in FIG. 12A. In this instance, the branch vessel 73 is smoothly guided to the pressing sections 110 by the guiding action of the inclined sections 112.

The branch vessel 73 having reached the pressing sections 110 is pressed against a wall surface opposed to pressing surfaces of the pressing sections 110 (in this embodiment, against the first inner surface 86a) by the pressing sections 110. Specifically, for example, the branch vessel 73 is sandwiched between the pressing sections 110 and the first inner surface 86a, and pressed flat in a radial direction. In this instance, since the first electrode 104 and the second electrode 106 are composed of elastic pieces, they are elastically deformed toward the second inner surface 88a side according to the outside diameter of the branch vessel 73, which helps enable the branch vessel 73 to be pressed effectively.

Figure 6B:
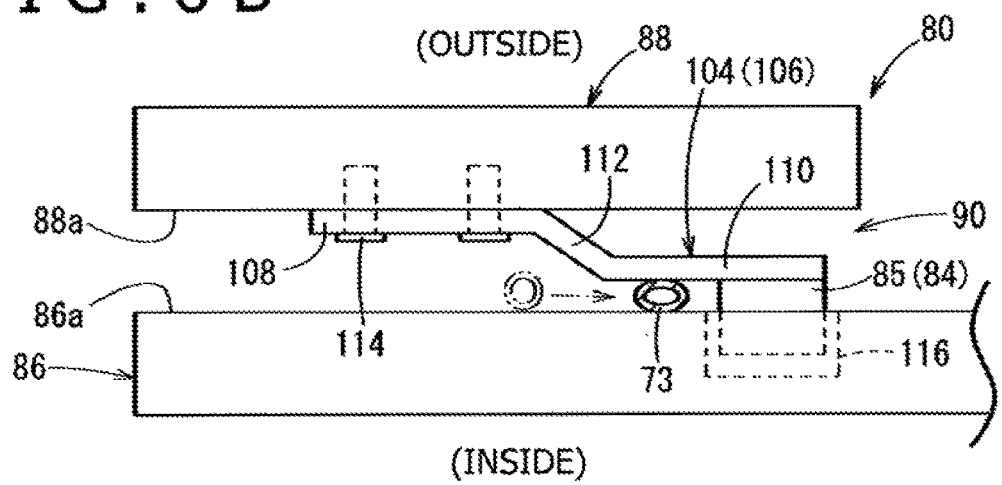
FIG. 6B is a schematic plan view of the side section with a thin branch vessel introduced in a slit.
Figure 6C:
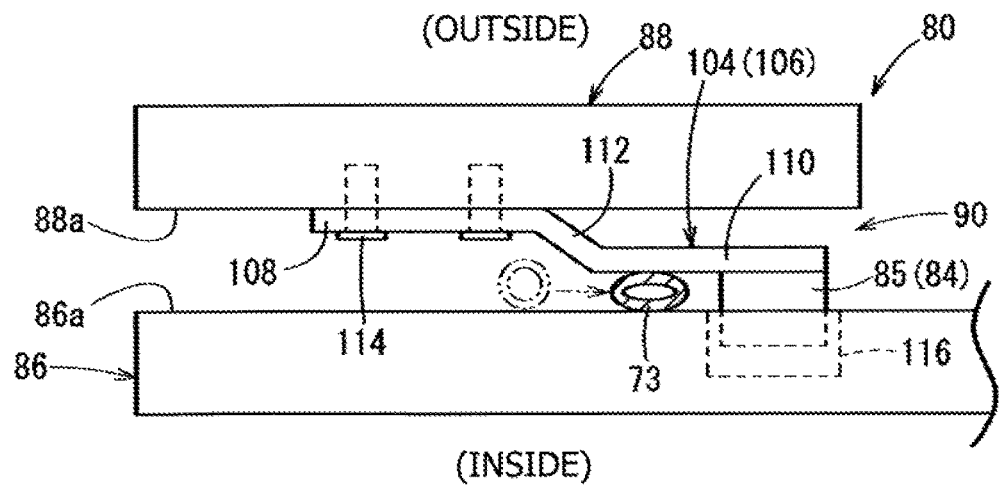
FIG. 6C is a schematic plan view of the side section with a thick branch vessel introduced in the slit.

In addition, as shown in FIGS. 6B and 6C, the first electrode 104 and the second electrode 106 change their elastic deformation amounts (warpage amounts) according to the outside diameter of the branch vessel 73, thereby automatically controlling their pressing forces. This helps ensure that in the case of a thin branch vessel 73 as depicted in FIG. 6B, the elastic deformation amounts of the first electrode 104 and the second electrode 106 are relatively small, and the pressing forces are relatively small. On the other hand, in the case of a thick branch vessel 73 as shown in FIG. 6C, the elastic deformation amounts of the first electrode 104 and the second electrode 106 are relatively large, and the pressing forces are relatively large.

Figure 12B:
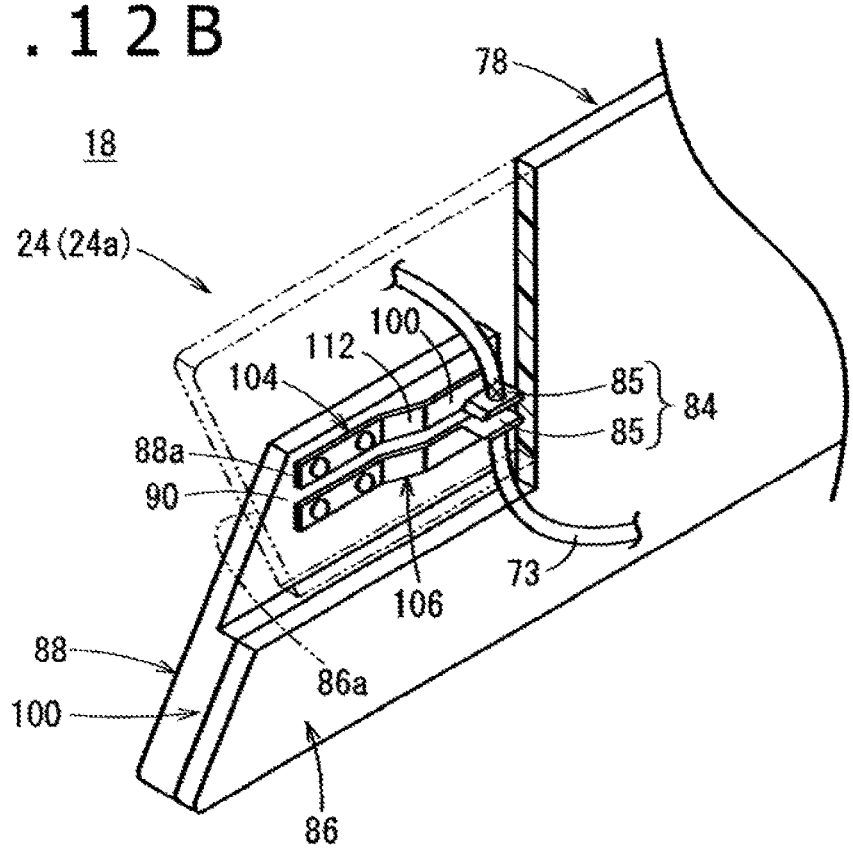
FIG. 12B is a fourth illustration for explaining the treatment of the branch vessel by the side section.

After the branch vessel 73 is thus put into a pressed state by the pressing sections 110 of the first electrode 104 and the second electrode 106, a high-frequency voltage is impressed between the first electrode 104 and the second electrode 106, whereby that portion of the branch vessel 73 which is located between the pressing sections 110 is cauterized. As a result, the branch vessel 73 is stanched. When the first dissecting device 12 is further moved forward, the branch vessel 73 is cut by the cutting section 84, as illustrated in FIG. 12B.

In this case, the branch vessel 73 introduced into the slit 90 can be observed (visually confirmed) from the inside of the dissecting member 18, through the transparent dissecting section main body 78 (in this embodiment, the first member 86), by the imaging device 17 (see FIG. 3) inserted in the cavity 28 of the base section 22. Therefore, the branch vessel 73 can be stanched and cut easily while observing the branch vessel 73.

Note that when the first dissecting device 12 is moved forward within the living body, the branch vessels 73 which do not contact the side sections 24 and are therefore not guided into the slit 90 by the introducing section 100 pass between the pair of side sections 24 and are neither stanched by the stanching section 80 nor cut by the cutting section 84.

Thus, according to the first dissecting device 12 provided with the side sections 24 (treating device), when the first dissecting device 12 is inserted into the living body and moved forward along the blood vessel 72, the tissue in the living body can be dissected by the dissecting section main body 78 and the branch vessels 73 embedded in the tissue can be easily captured. In addition, since the branch vessel 73 introduced into the slit 90 via the dissecting section main body 78 is cauterized while pressed by the stanching section 80, even a thin branch vessel 73 can be reliably stanched. Further, since the cauterized branch vessel 73 is cut by the cutting section 84, the stanched branch vessel 73 can be reliably cut.

Since at least a part of the stanching section 80 is adapted to be displaceable in the separating direction of the first inner surface 86a and the second inner surface 88a, the branch vessel 73 introduced into the slit 90 can be effectively pressed, regardless of the thickness (diametric size) of the blood vessel. Particularly, for example, since the stanching section 80 having the form of a leaf spring is elastically deformed attendant on the introduction of the branch vessel 73 into the slit 90, the branch vessel 73 can be pressed with an appropriate pressing force.

In addition, since the stanching section 80 can include the stationary section 108 and the pressing section 110 on the free end side, the pressing section 110 can be displaced with the stationary section 108 as a center for displacement. Therefore, the branch vessel 73 can be suitably pressed by the pressing section 110. Moreover, since the stanching section 80 is provided, between the stationary section 108 and the pressing section 110, with the inclined section 112 inclined toward the side of one of the first inner surface 86a and the second inner surface 88a, the branch vessel 73 can be smoothly introduced into the pressing section 110 under the guiding action of the inclined section 112.

In addition, since the first electrode 104 and the second electrode 106 are juxtaposed while spaced apart from each other in the direction perpendicular to the forward-backward direction of the side sections 24, the branch vessel 73 introduced into the slit 90 in the state of extending in a direction intersecting the extending direction of the slit 90 can be securely supplied with an electric current and cauterized.

Since the first electrode 104 and the second electrode 106 are fixed to the same side of the first inner surface 86a and the second inner surface 88a, the branch vessel 73 can be suitably pressed, by the first electrode 104 and the second electrode 106, toward the inner surface opposed to the inner surface onto which the first electrode 104 and the second electrode 106 are fixed.

Since the cutting section 84 is projectingly provided at the stanching section 80, the branch vessel 73 stanched by the stanching section 80 can be suitably cut. In addition, since the cutting section 84 is formed integral with the stanching section 80, the number of component parts constituting the cutting section 84 and the stanching section 80 can be reduced.

Since the dissecting section main body 78 is provided at its distal portion with the introducing section 100 which communicates with the slit 90 and the opening width of which decreases in the proximal direction, the branch vessel 73 can be smoothly guided into the slit 90.

The slit 90 can include the first slit element 90a along the thickness direction of the dissecting section main body 78, and the second slit element 90b which intersects the first slit element 90a. Therefore, for example, by a method wherein the first member 86 and the second member 88 one of which is formed with a slit-shaped thin groove are laid on each other and joined together, it is possible to easily construct the dissecting section main body 78 formed with the slit 90 into which the branch vessel 73 is to be introduced.

After the first dissecting device 12 is moved forward by a distance corresponding to the required length, the first dissecting device 12 is drawn out of the living body via the incision 71 shown in FIG. 8.

Next, the fat 74 present on the lower side (a fascia 76 side) of the blood vessel 72 exposed through the incision 71 is dissected. In this case, for example, the fat 74 can be dissected by a technician's hand or by use of an appropriate device. Subsequently, the second dissecting device 14 with the imaging device 17 inserted therein is inserted via the incision 71, and the second dissecting device 14 is disposed on the lower side of the blood vessel 72. Note that the second dissecting device 14 may be preliminarily provided with the imaging device 17 as a component thereof.

Figure 13:
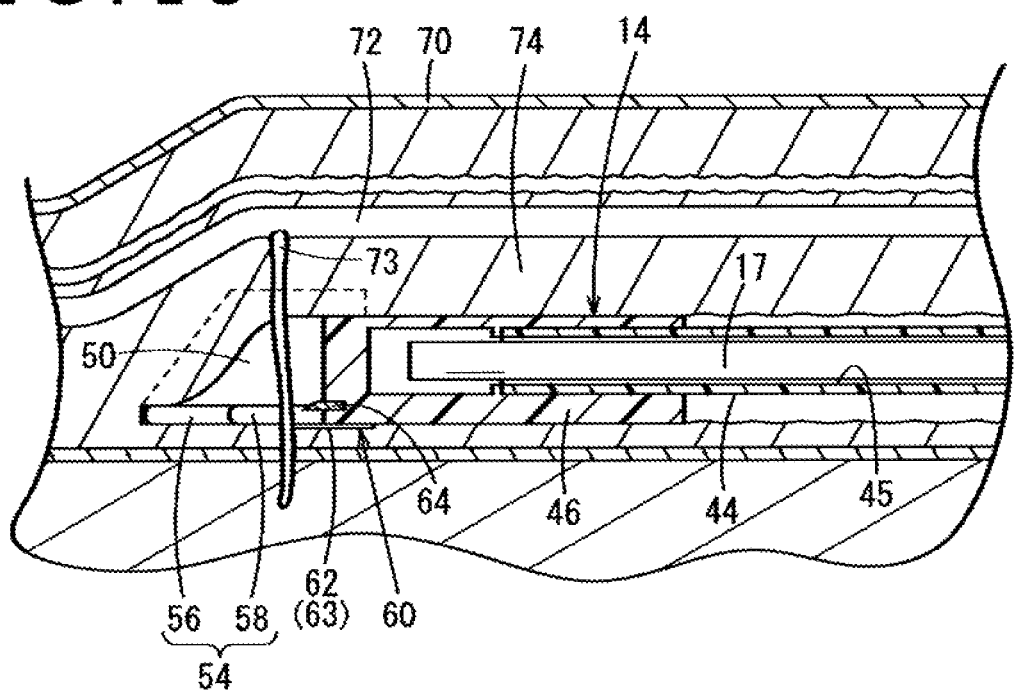
FIG. 13 is a sectional view along an extending direction of a blood vessel in a living body, for explaining a state in which the second dissecting device is moved forward in the living body along the blood vessel.

Then, the second dissecting device 14 is pushed forward in the living body along the blood vessel 72 by a distance corresponding to the required length (the length to be harvested). In this case, as depicted in FIG. 13, the second dissecting device 14 is moved forward while dissecting the fat 74 on the lower side of the blood vessel 72 by the dissecting section 50 of the dissecting member 46. Specifically, the dissecting section 50 dissects the fat 74 on the lower side of the blood vessel 72 in the thickness direction of the dissecting member 46 (in the direction of alignment of the dissecting member 46 with the blood vessel 72). As a result, a dissected part is formed in such a manner as to surround the whole circumference of the blood vessel 72. Specifically, for example, the fat 74 can be dissected in the whole circumferential range of the perimeter of the blood vessel 72.

In addition, when the second dissecting device 14 is moved forward within the living body along the blood vessel 72, as shown in FIG. 13, the second dissecting device 14 guides the branch vessel 73 to the treating section 60 by the blood vessel guide passage 54, and stanches and cuts the branch vessel 73 by the treating section 60. Specifically, for example, the branch vessel 73 branched to the lower side from the blood vessel 72 is drawn near by the first groove section 56 of the blood vessel guide passage 54. In addition, the branch vessel 73 is guided to the treating section 60 by the second groove section 58. Then, the branch vessel 73 guided to the treating section 60 is stanched (cauterized) by the stanching section 62, and is thereafter cut by the cutting section 64.

After the second dissecting device 14 is moved forward by the distance corresponding to the required length, the second dissecting device 14 is drawn out of the living body via the incision 71.

By these operations, the dissecting step of dissecting the blood vessel 72 in the state of being covered with the surrounding fat 74 (tissue) is completed.

Figure 14A:
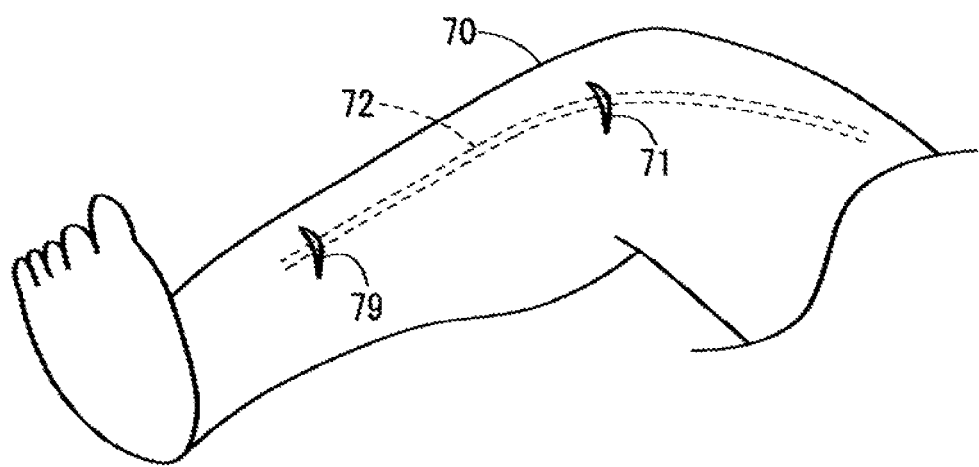
FIG. 14A illustrates cutting of a blood vessel to be harvested.

Next, the cutting step is conducted, in the cutting step, as depicted in FIG. 14A, the skin 70 is incised at a position spaced from the incision 71 by a distance corresponding to the length of the blood vessel 72 to be harvested, to form an incision 79, whereby the blood vessel 72 is exposed at the incision 79. Then, by way of the two incisions 71 and 79, both ends of that part of the blood vessel 72 which is to be harvested are ligated, after which the blood vessel 72 is cut.

Figure 14B:
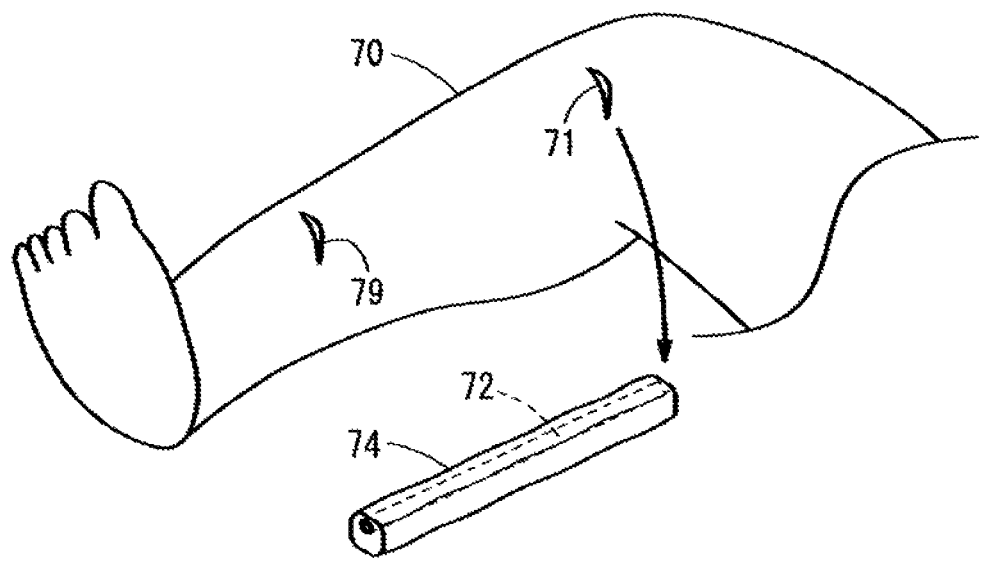
FIG. 14B illustrates extraction of the blood vessel accompanied with fat from the inside of a living body.

When the cutting step has been completed, the extracting step is performed next. In the extracting step, as shown in FIG. 14B, the blood vessel 72 accompanied with the fat 74 is extracted to the outside of the living body, through the incision 71 or the incision 79.

By the dissecting step, cutting step and extracting step as described above, the blood vessel 72 accompanied with the fat 74 can be harvested from the living body. According to such a method, the blood vessel 72 can be harvested smoothly and with low invasion. In addition, since the dissecting step can be carried out without cutting the blood vessel 72, it is possible to let blood flow in the blood vessel 72 for a prolonged time. Consequently, the blood vessel 72 kept in an ischemic state for a shorter time and accompanied with less damage can be harvested.

In addition, the blood vessel 72 covered with the fat 74 is characterized in that lowering of blood flow due to expansion or bending can be inhibited, damage to endotheliocyte, smooth muscle, and nutrient vessels (a network of small blood vessels) can be reduced, and thickening of the blood vessel wall can be suppressed. Therefore, the use of the blood vessel 72 covered with the fat 74 as a bypass vessel offers an excellent long-term patency rate. Particularly, for example, since the blood vessel 72 accompanied with the fat 74 thus harvested has nutrient vessels remaining in the blood vessel wall or the fat 74, it is considered that nutrients are supplied to the blood vessel 72 serving as the bypass vessel after bypass grafting, so that the above-mentioned effects can be enhanced.

The order in which the first dissecting device 12 and the second dissecting device 14 are used may be reverse to that in the above description. Specifically, for example, a sequence may be adopted in which the second dissecting device 14 is first inserted into the living body and moved forward along the blood vessel 72, then the second dissecting device 14 is drawn out of the living body, and thereafter the first dissecting device 12 is inserted into the living body and moved forward along the blood vessel 72.

The second incision 79 may be formed simultaneously with the first incision 71. Alternatively, the second incision 79 may be formed after the first device (the first dissecting device 12, in the case of using the first dissecting device 12 and the second dissecting device 14 in this order) is inserted into the living body (in the period until the insertion of the second one of the two dissecting devices into the living body).

In the dissecting step, the first device may be taken out via the second incision 79. In addition, the second device (the second dissecting device 14, in the case of using the first dissecting device 12 and the second dissecting device 14 in this order) may be inserted by way of the second incision 79.

Figure 15:
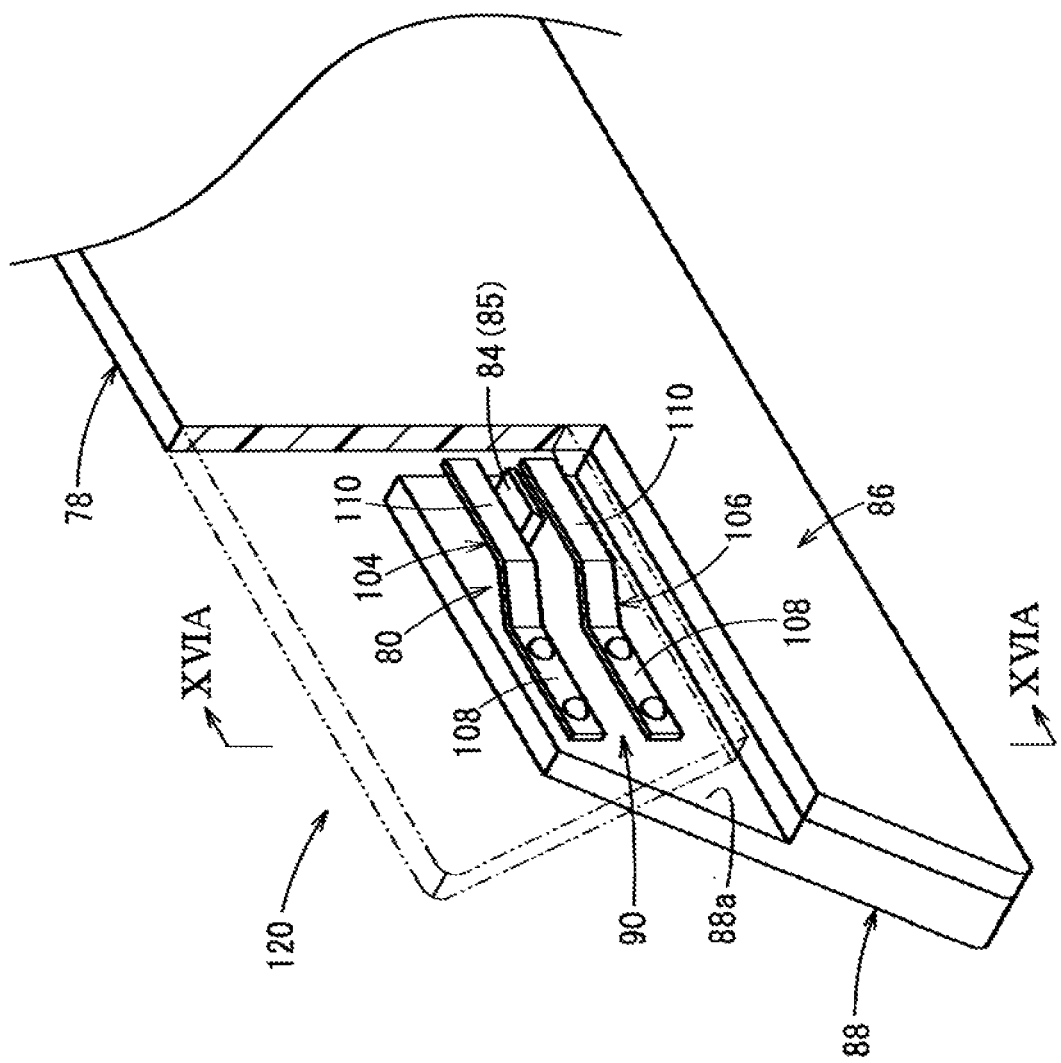
FIG. 15 is a perspective view of a side section according to a first modification.
Figure 16A:
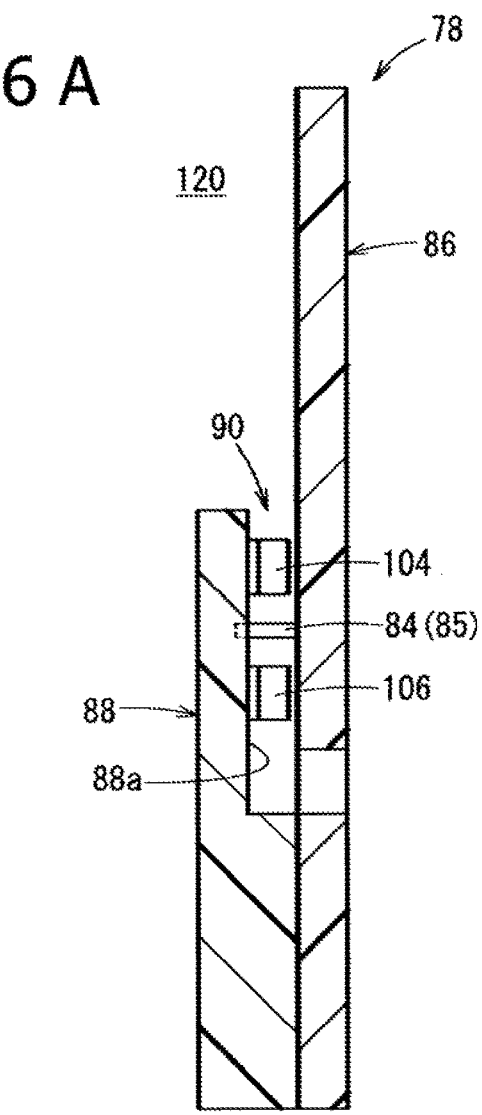
FIG. 16A is a sectional view of the side section according to the first modification, taken along line XVIA-XVIA of FIG. 15.
Figure 16B:
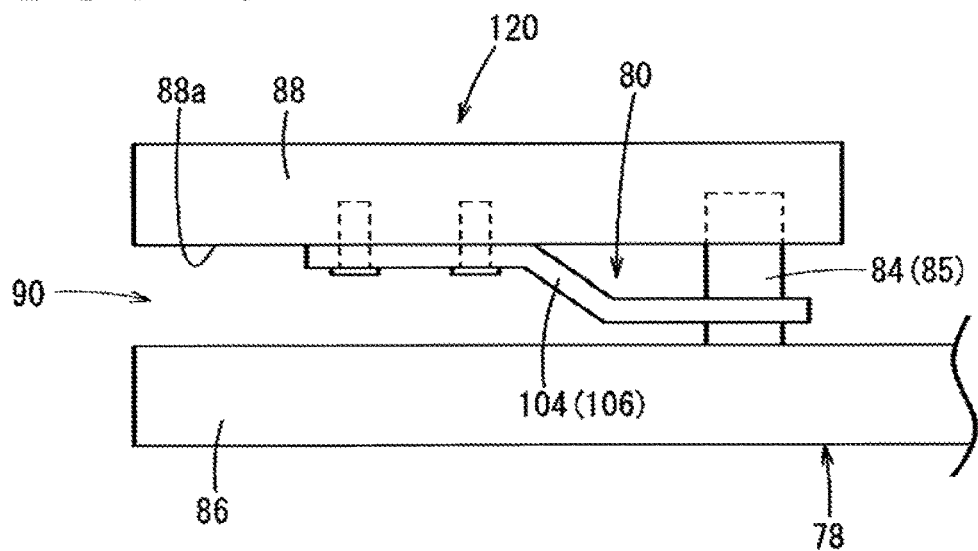
FIG. 16B is a schematic plan view of the side section according to the first modification.

In the dissecting device 18 as described above, a side section 120 according to a modification shown in FIGS. 15 to 16B may be adopted in place of the side section 24. In this side section 120, the cutting section 84 is fixed not to the stanching section 80 but to the dissecting section main body 78 (specifically, for example, to the second inner surface 88a). Specifically, for example, the cutting section 84 and the stanching section 80 are configured as separate component parts. In this configuration, the cutting section 84 is composed of a single cutter piece 85, which is disposed between the pressing sections 110 of the first electrode 104 and the second electrode 106 that are juxtaposed while spaced apart in parallel to each other.

The cutting section 84 may be disposed on the proximal side of the pressing section 110, inside the slit 90. The cutting section 84 may be fixed to the first inner surface 86a, or may be fixed to both of the first inner surface 86a and the second inner surface 88a.

The side sections 24 and 120 as described above are each configured as part of the dissecting member 18 having the base section 22. Since the side section 24 is configured to be able to dissect tissue and to stanch and cut the branch vessel 73, however, the side section 24 may be configured as a treating device in the form of being separate from the base section 22. In this case, the grasping section 16 is preferably connected to a proximal portion of the dissecting section main body 78. By inserting and moving forward such a treating device into the living body plural times and sequentially dissecting different regions in the circumferential direction of the blood vessel 72, it is possible to dissect the fat 74 in the whole circumferential range of the perimeter of the blood vessel 72.

In the dissecting member 18 described above, a side section 122 depicted in FIGS. 17 to 20 may be adopted in place of the side section 24. Note that for easy understanding, part of the first member 86 is drawn in imaginary line in FIGS. 17 and 20.

Figure 17:
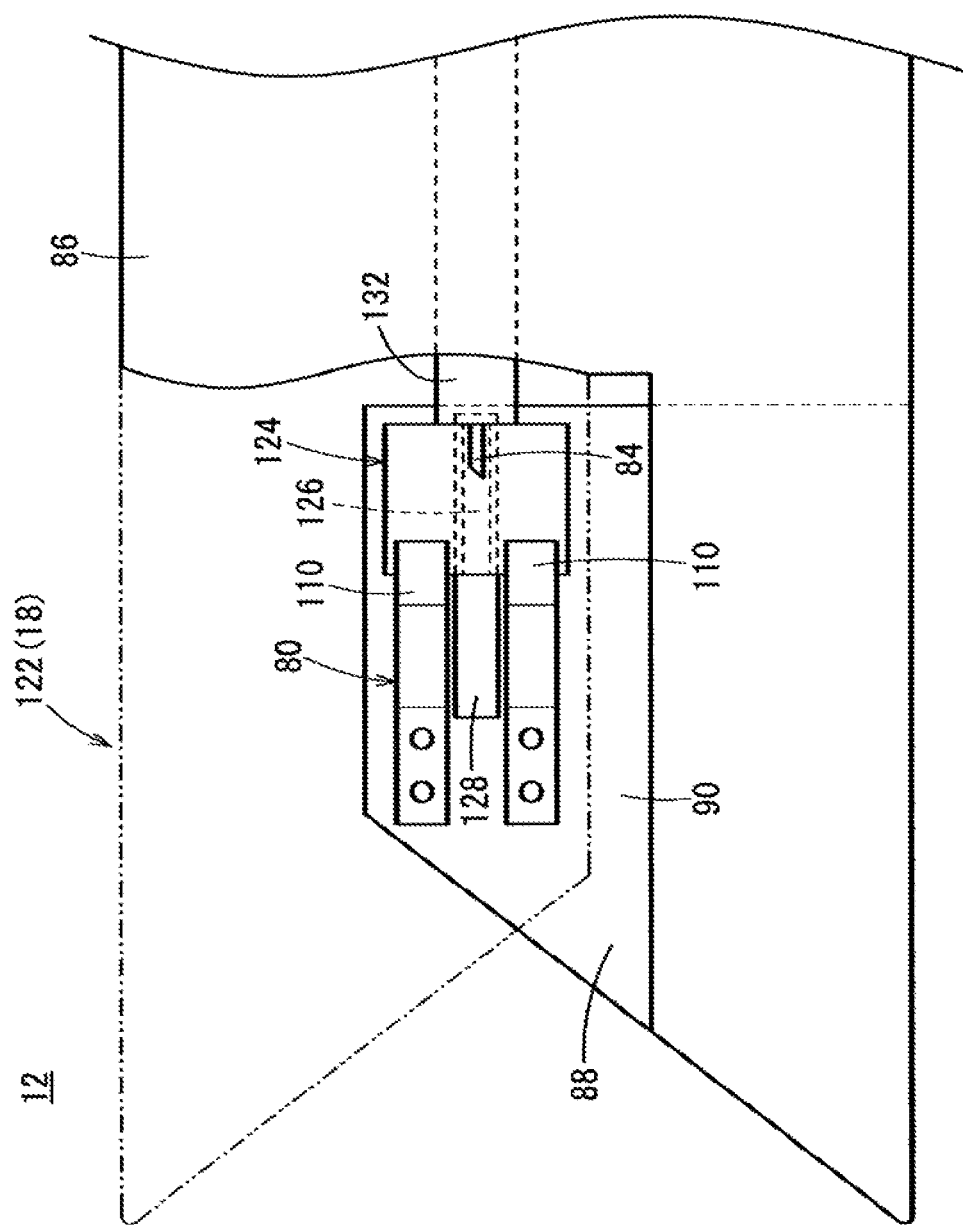
FIG. 17 is a side view of a side section according to a second modification.
Figure 18:
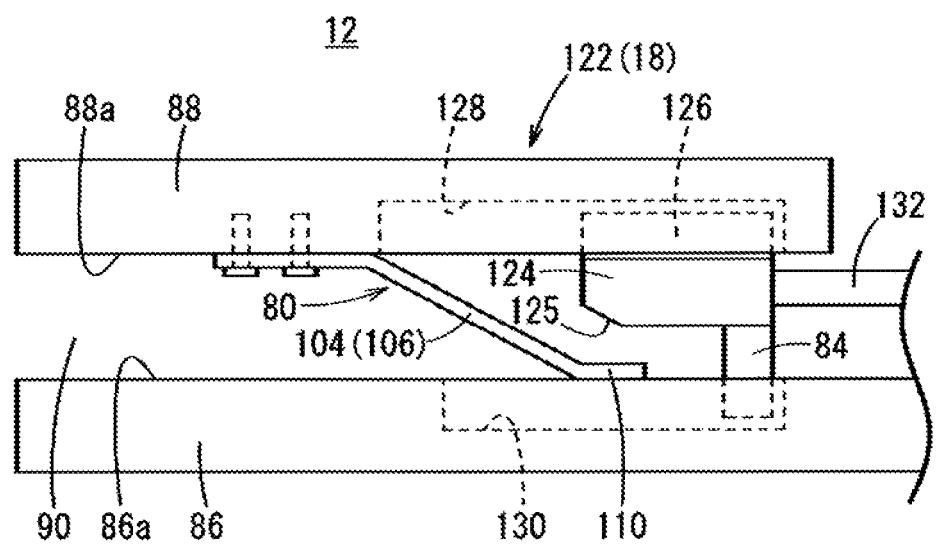
FIG. 18 is a schematic plan view of the side section according to the second modification.

In FIGS. 17 and 18, the side section 122 further can include a pressing member 124, in addition to the stanching section 80 and the cutting section 84, as a treating mechanism for treating the branch vessel 73 introduced into the slit 90. The pressing member 124 is displaceably disposed in the slit 90, and is configured in such a manner that attendant on a displacement thereof, it presses the stanching section 80 in a direction for the stanching section 80 to press the branch vessel 73.

Specifically, for example, in the side section 122 in the illustrated example, the pressing member 124 is displaceable along the axial direction of the side section 122 (the axial direction of the dissecting member 18), and, attendant on the displacement in the axial direction, it presses the stanching section 80 (the pressing sections 110 of the first electrode 104 and the second electrode 106) toward the first inner surface 86a side. The pressing member 124 can be formed of an insulating material such that it does not cause short-circuiting between the first electrode 104 and the second electrode 106 when making contact with the electrodes. The pressing member 124 is formed, on the first inner surface 86a side of a distal portion thereof, with a tapered surface 125, which is inclined relative to a moving direction of the pressing member 124.

The pressing member 124 is formed with a guide projection 126. The guide projection 126 projects from the pressing member 124 to the second member 88 side (the side opposite to the direction in which the pressing member 124 presses the stanching section 80). The second inner surface 88a of the second member 88 is formed with a guide groove 128, which extends in the axial direction of the side section 122. The guide projection 126 is slidably inserted in the guide groove 128, which helps enable the pressing member 124 to be displaced in the axial direction within the slit 90, under a guiding action of the guide projection 126 and the guide groove 128.

A driving member 132 for moving the pressing member 124 in the axial direction is connected to the pressing member 124. The driving member 132 is connected to an operating member (not shown) on the user's side of the first dissecting device 12 (at a proximal portion of the grasping section 16). By operating the operating member, the user can move the pressing member 124 connected to the driving member 132 in the axial direction.

In addition, the pressing member 124 is provided with a cutting section 84 (cutter). The cutting section 84 projects from the pressing member 124 toward the first member 86 side (in the direction for the pressing member 124 to press the stanching section 80). The first inner surface 86a of the first member 86 is formed with a groove section 130 extending along the axial direction of the side section 122. A portion of the cutting section 84 (an end portion on the side of projecting from the pressing member 124 of the cutting section 84) is inserted in the groove section 130. The other portion of the cutting section 84 (that portion of the cutting section 84 which is located between the pressing member 124 and the first inner surface 86a) is exposed to the inside of the slit 90.

When the first dissecting device 12 having the side section 122 configured as above is moved forward in the living body along the blood vessel 72, the first dissecting device 12 guides the branch vessel 73 branched from the blood vessel 72 into the slit 90 through the introducing section 100, and stanches and cuts the branch vessel 73 by the stanching section 80, the cutting section 84 and the pressing member 124 which are provided at the slit 90.

Figure 19A:
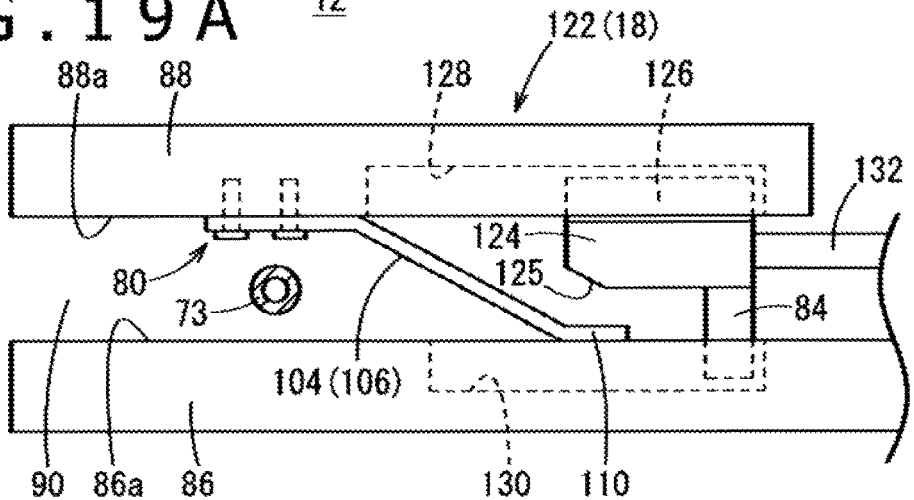
FIG. 19A is a first illustration for explaining a treatment of a branch vessel by the side section according to the second modification.
Figure 19B:
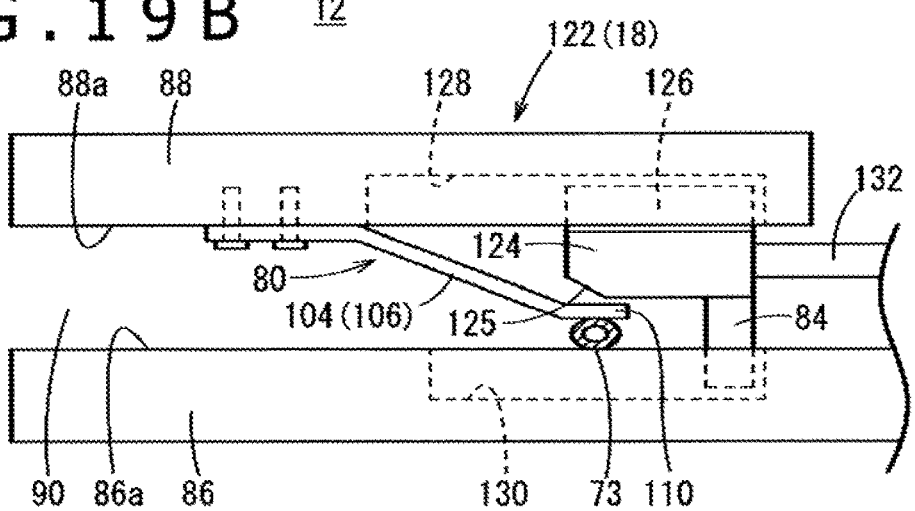
FIG. 19B is a second illustration for explaining the treatment of the branch vessel by the side section according to the second modification.

Specifically, for example, first, as shown in FIG. 19A, attendant on forward movement of the side section 122 in the living body, the branch vessel 73 is introduced into the slit 90. Then, when the side section 122 is further moved forward, the branch vessel 73 reaches the pressing sections 110 of the first electrode 104 and the second electrode 106, as depicted in FIG. 19B. The branch vessel 73 having reached the pressing sections 110 is pressed against a wall surface opposed to the pressing surfaces of the two pressing sections 110 (in this embodiment, against the first inner surface 86a) by the pressing sections 110 which have the form of leaf springs. As a result, the branch vessel 73 is sandwiched between the two pressing sections 110 and the first inner surface 86a and pressed flat in a radial direction.

Figure 19C:
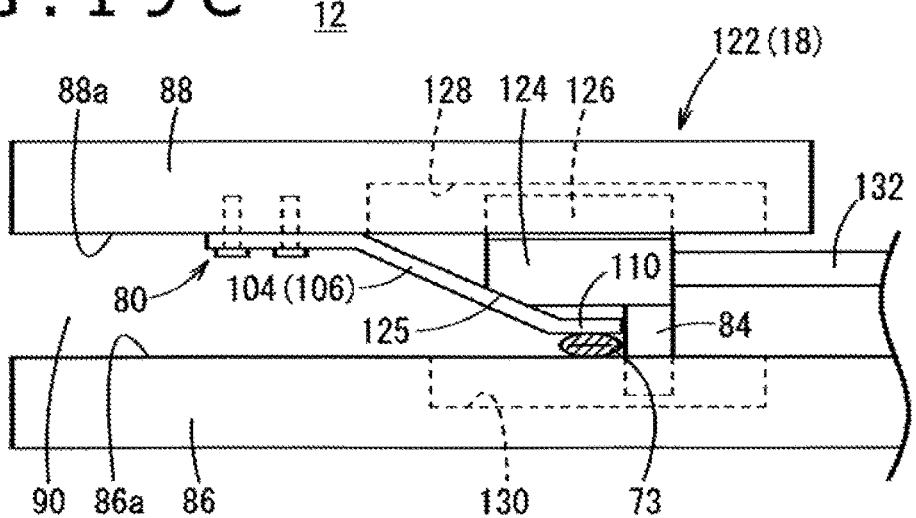
FIG. 19C is a third illustration for explaining the treatment of the branch vessel by the side section according to the second modification.

Next, the user moves the pressing member 124 distally through the driving member 132 as illustrated in FIG. 19C. Attendant on the distal movement, the pressing member 124 presses the cutting section 84 (the first electrode 104 and the second electrode 106) toward the first inner surface 86a side. This causes the branch vessel 73 sandwiched between the cutting section 84 and the first inner surface 86a to be further pressed flat in the radial direction. As a result, the branch vessel 73 is put into a sufficiently pressed flat state.

Then, a high-frequency voltage is impressed between the first electrode 104 and the second electrode 106, whereby that portion of the branch vessel 73 which is located between the pressing sections 110 is cauterized. As a result, the branch vessel 73 is stanched. Next, as shown in FIG. 20, the user moves the pressing member 124 further forward in a distal direction, thereby cutting the cauterized branch vessel 73 by the cutting section 84. Specifically, for example, since the cutting section 84 is provided in the pressing member 124, the cutting section 84 is also moved distally as the pressing member 124 is moved distally. In this instance, the cutting section 84 enters between the first electrode 104 and the second electrode 106, and cuts the cauterized branch vessel 73. After the branch vessel 73 is thus cut, the pressing member 124 is moved proximally (moved backward), whereby the pressing member 124 is returned into its original position. Note that the cutting of the branch vessel 73 by the cutting section 84 may be conducted while cauterizing the branch vessel 73.

According to the side section 122 (treating device) configured as above, the stanching section 80 in the state of pressing the branch vessel 73 is pressed by the pressing member 124, whereby the branch vessel 73 can be sufficiently pressed flat in the radial direction. Then, by cauterizing the branch vessel 73 thus sufficiently pressed flat, it is possible to reliably stanch the branch vessel 73.

In addition, in the side section 122, the cutting section 84 is provided in the pressing member 124, and is displaced together with the pressing member 124 when the pressing member 124 is displaced. Owing to this configuration, it is unnecessary to displace the pressing member 124 and the cutting section 84 by individual operations; thus, the pressing of the stanching section 80 by the pressing member 124 and the cutting of the branch vessel 73 by the cutting section 84 can be easily carried out by a series of operations.

Figure 21:
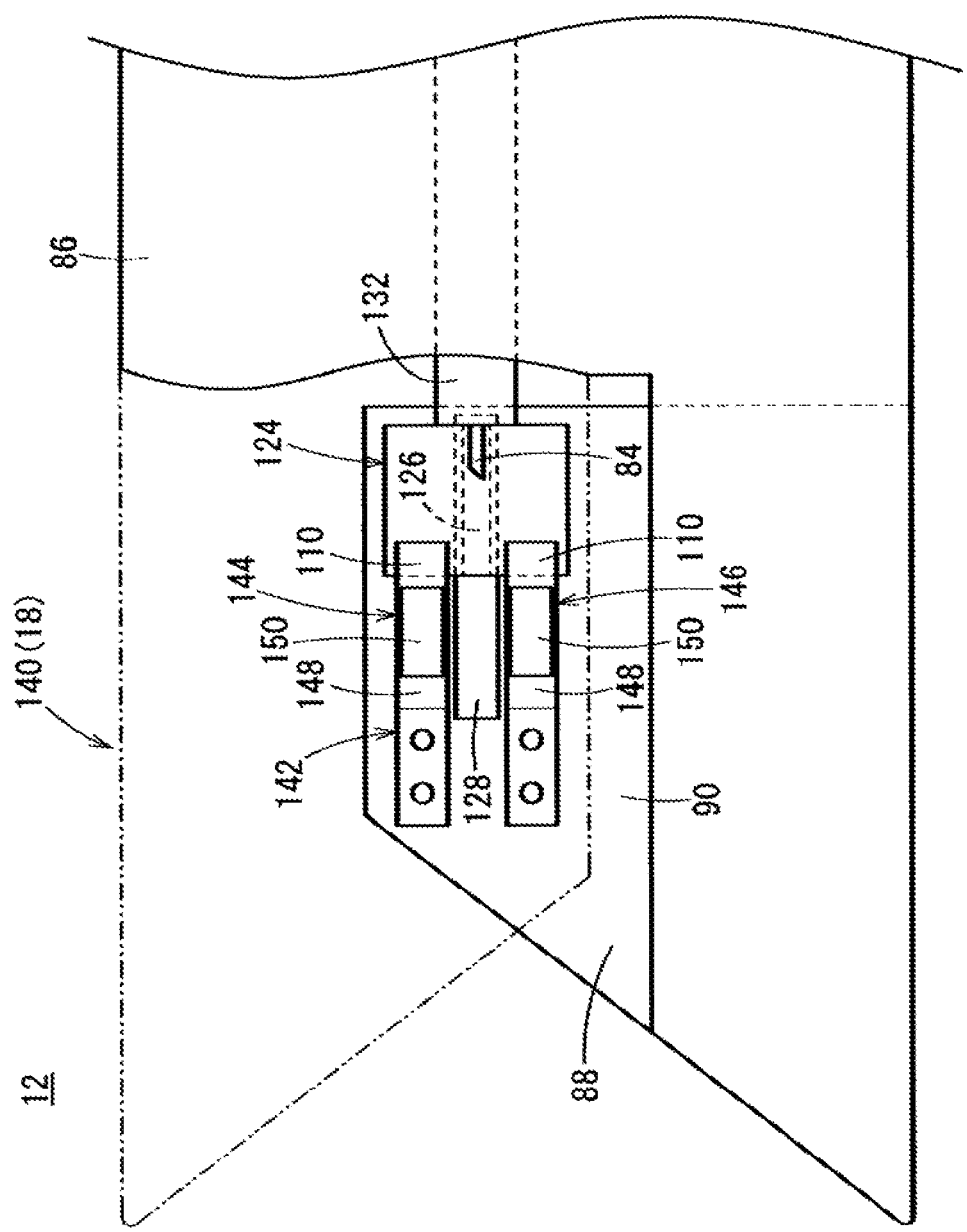
FIG. 21 is a side view of the side section according to the third modification.
Figure 22:
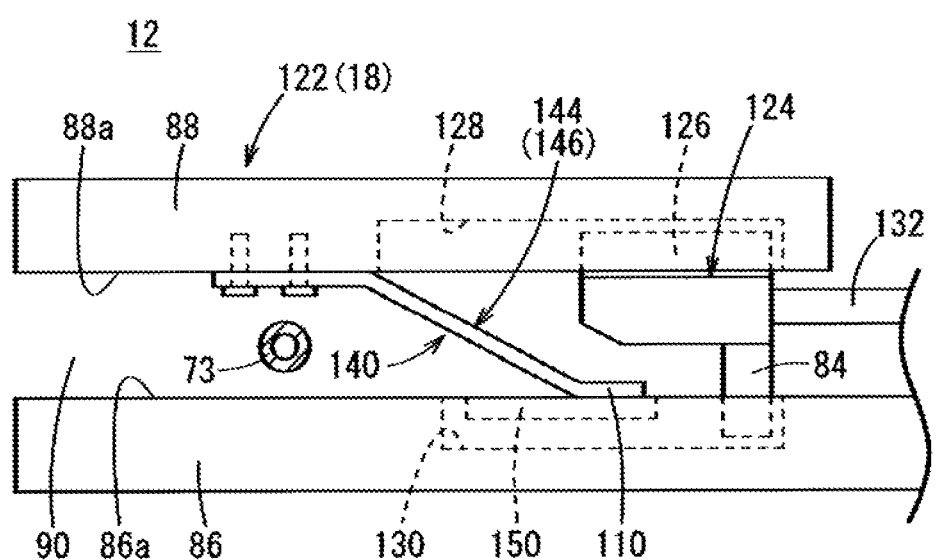
FIG. 22 is a schematic plan view of the side section according to the third modification.

In the dissecting member 18 as above, a side section 140 depicted in FIGS. 21 and 22 may be adopted in place of the side section 24. Note that for easy understanding, part of the first member 86 is drawn in imaginary line in FIG. 21.

In accordance with an exemplary embodiment, like the side section 122 described above, the side section 140 can further include the pressing member 124 in addition to a stanching section 142 and the cutting section 84, as a treating mechanism for treating the branch vessel 73 introduced into the slit 90. In the side section 140, the stanching section 142 has a first bipolar electrode section 144 and a second bipolar electrode section 146. The first bipolar electrode section 144 and the second bipolar electrode section 146 are disposed spaced apart in a direction (the vertical direction in FIG. 21) perpendicular to the axial direction of the side section 140.

Each of the first bipolar electrode section 144 and the second bipolar electrode section 146 can include a spring electrode 148 which can be displaced by elastic deformation of at least part thereof in the slit 90, and a counter electrode 150 disposed opposite to the spring electrode 148. The spring electrode 148 is configured in the same manner as the above-mentioned first electrode 104 and the second electrode 106, and is fixed to the second member 88 in the illustrated example. The counter electrode 150 is an electrode to be paired with the spring electrode 148, and is fixed to the first member 86 in the illustrated example. Note that the counter electrode 150 is disposed at a position different from that of the groove section 130 (see FIG. 22).

When the first dissecting device 12 having the side section 140 configured as above is moved forward in the living body along the blood vessel 72, the branch vessels 73 are introduced into the slit 90. When the side section 140 is moved further forward, the branch vessel 73 is sandwiched between the spring electrode 148 and the counter electrode 150, at each of the first bipolar electrode section 144 and the second bipolar electrode section 146, and is pressed flat in a radial direction. Then, when the user moves the pressing member 124 distally, the pressing member 124 presses the spring electrodes 148 of the first bipolar electrode section 144 and the second bipolar electrode section 146 toward the branch vessel 73 side. As a result, the branch vessel 73 is further pressed flat in the radial direction. Then, at each of the first bipolar electrode section 144 and the second bipolar electrode section 146, a high-frequency voltage is impressed between the spring electrode 148 and the counter electrode 150, whereby that portion of the branch vessel 73, which is located between the spring electrode 148 and the counter electrode 150, is cauterized. As a result, the branch vessel 73 is stanched. The operations conducted subsequently are the same as those in the case of the side section 122 described above.

The present disclosure is not limited to the above-described embodiments, and various modifications are possible without departing from the spirit or scope of the gist of the present disclosure.

The detailed description above describes a treatment device for dissecting tissue such as fat in a living body and stanching and cutting a blood vessel. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A treatment device comprising:
   a dissecting section main body which is configured to dissect tissue in a living body when inserted into the living body along a blood vessel, and which has a slit permitting a branch vessel branched from the blood vessel to enter into the slit;
   a stanching section which is disposed at the slit and which presses and cauterizes the branch vessel introduced into the slit, at least a part of the stanching section configured to be displaceable in a separating direction of a first inner surface and a second inner surface, wherein the first inner surface and the second inner surface face each other and define the slit, and the stanching section includes a stationary section fixed on one of the first inner surface and the second inner surface, and a pressing section disposed between the first inner surface and the second inner surface and which constitutes a free end on a proximal side of the stationary section, and wherein the free end on the proximal side of the stationary section is configured to contact the blood vessel; and
   a cutting section which is disposed at the slit and which cuts the cauterized branch vessel.

2. The treatment device according to claim 1,
   wherein the stanching section has, between the stationary section and the pressing section, an inclined portion inclined toward one of the first inner surface and the second inner surface.

3. The treatment device according to claim 1,
   wherein the stanching section includes a first electrode and a second electrode, which constitute bipolar electrodes.

4. The treatment device according to claim 3, wherein the cutting section comprises two cutter pieces, one of the two cutter pieces provided on the first electrode and another of the two cutter pieces provided on the second electrode.

5. The treatment device according to claim 4, wherein the two cutter pieces project from the first and the second electrodes toward a side of the first inner surface and a side of the second inner surface onto which the first electrode and the second electrode are not fixed, respectively.

6. The treatment device according to claim 1,
   wherein the cutting section is projectingly provided at the stanching section.

7. The treatment device according to claim 1, comprising:
   a pressing member configured to be displaceably disposed in the slit and which, attendant on displacement of the pressing member, presses the stanching section in a direction for the stanching section to contact the branch vessel.

8. The treatment device according to claim 7, wherein the cutting section is provided in the pressing member and is displaced together with the pressing member when the pressing member is displaced.

9. A treatment device comprising:
   a dissecting section main body which is configured to dissect tissue in a living body when inserted into the living body along a blood vessel, and which has a slit permitting a branch vessel branched from the blood vessel to enter into the slit;
   a stanching section which is disposed at the slit and which presses and cauterizes the branch vessel introduced into the slit, wherein at least a part of the stanching section is configured to be displaceable in a separating direction of a first inner surface and a second inner surface, wherein the first inner surface and the second inner surface face each other and define the slit, and wherein the stanching section includes a first electrode and a second electrode which constitute bipolar electrodes, and wherein the stanching section includes a stationary section fixed on one of the first inner surface and the second inner surface, and a pressing section disposed between the first inner surface and the second inner surface and having a free end on a proximal side of the stationary section and configured to contact the blood vessel; and
a cutting section which is disposed at the slit and which cuts the cauterized branch vessel.

10. The treatment device according to claim 9, wherein the stanching section has, between the stationary section and the pressing section, an inclined portion inclined toward one of the first inner surface and the second inner surface.

11. The treatment device according to claim 9, wherein the cutting section is projectingly provided at the stanching section.

12. The treatment device according to claim 9, further comprising:
a pressing member configured to be displaceably disposed in the slit and which, attendant on displacement of the pressing member, presses the stanching section in a direction for the stanching section to contact the branch vessel.

13. The treatment device according to claim 12, wherein the cutting section is provided in the pressing member and is displaced together with the pressing member when the pressing member is displaced.

14. The treatment device according to claim 9, wherein the cutting section comprises a first cutter piece provided on the first electrode and a second cutter piece provided on the second electrode.

15. A method for dissecting tissue, the method comprising:
introducing a dissecting device having a dissecting section main body which is configured to dissect tissue into a living body along a blood vessel, the dissecting device having a slit, which permits a branch vessel branched from the blood vessel to enter into the slit;
cauterizing the branch vessel introduced into the slit in a stanching section which is disposed at the slit, and wherein at least a part of the stanching section is configured to be displaceable in a separating direction of a first inner surface and a second inner surface, wherein the first inner surface and the second inner surface face each other and define the slit, the stanching section including a stationary section fixed on one of the first inner surface and the second inner surface;
contacting the blood vessel with a pressing section disposed between the first inner surface and the second inner surface and which constitutes a free end on a proximal side of the stationary section; and
cutting the cauterized branch vessel with a cutting section which is disposed at the slit.

16. The method according to claim 15, wherein the stanching section has, between the stationary section and the pressing section, an inclined portion inclined toward one of the first inner surface and the second inner surface, and the stanching section including a first electrode and a second electrode which constitute bipolar electrodes.

17. The method according to claim 16, wherein the cutting section comprises two cutter pieces, one of the two cutter pieces provided on the first electrode and another of the two cutter pieces provided on the second electrode.

18. The method according to claim 15, wherein the cutting section is projectingly provided at the stanching section.

19. The method according to claim 15, comprising:
pressing the stanching section in a direction for the stanching section to contact the branch vessel with a pressing member which is displaceably disposed in the slit and which, attendant on displacement of the pressing member.

20. The method according to claim 19, comprising:
displacing the cutting section in the pressing member together with the pressing member when the pressing member is displaced.

* * * * *